US011766081B2

(12) United States Patent
Thomas

(10) Patent No.: US 11,766,081 B2
(45) Date of Patent: *Sep. 26, 2023

(54) EASY ACCESS APPAREL

(71) Applicant: HACKENSACK MERIDIAN HEALTH, INC., Edison, NJ (US)

(72) Inventor: Charles Augustus Thomas, Teaneck, NJ (US)

(73) Assignee: HACKENSACK MERIDIAN HEALTH, INC., Edison, NJ (US)

(*) Notice: Subject to any disclaimer, the term of this patent is extended or adjusted under 35 U.S.C. 154(b) by 475 days.

This patent is subject to a terminal disclaimer.

(21) Appl. No.: 16/428,298

(22) Filed: May 31, 2019

(65) Prior Publication Data

US 2019/0364992 A1    Dec. 5, 2019

Related U.S. Application Data

(60) Provisional application No. 62/680,848, filed on Jun. 5, 2018.

(51) Int. Cl.
*A41D 13/12* (2006.01)
*A61F 13/53* (2006.01)
*A61F 13/15* (2006.01)

(52) U.S. Cl.
CPC ..... *A41D 13/1281* (2013.01); *A41D 13/1245* (2013.01); *A41D 13/1254* (2013.01); *A61F 13/53* (2013.01); *A61F 2013/15154* (2013.01); *A61F 2013/530007* (2013.01)

(58) Field of Classification Search
CPC ............ A41D 13/1236; A41D 13/1245; A41D 13/1281; A41D 13/1254; A41D 13/1263; A41D 13/129; A61F 13/53
See application file for complete search history.

(56) References Cited

U.S. PATENT DOCUMENTS

| | | | |
|---|---|---|---|
| 1,489,046 A * | 4/1924 | Thompson | A41B 9/08 2/269 |
| 3,336,923 A * | 8/1967 | Devaud | A61F 13/51121 604/370 |
| 4,805,241 A * | 2/1989 | Faccini | A41D 13/1236 2/119 |
| 5,045,322 A | 9/1991 | Blank et al. | |
| 5,326,305 A * | 7/1994 | Fochler | A61F 13/145 2/267 |
| 5,674,214 A | 10/1997 | Visscher et al. | |
| 5,802,611 A * | 9/1998 | McKenzie | A41D 13/1236 2/69 |
| 6,048,252 A * | 4/2000 | Sebring | A41C 3/148 450/1 |

(Continued)

OTHER PUBLICATIONS

Rupp, SM, et al. Practice Guidelines for Central Venous Access A Report by the American Society of Anesthesiologists Task Force on Central Venous Access. Anesthesiology 2012; 116:539-73.

(Continued)

*Primary Examiner* — Alissa L Hoey
(74) *Attorney, Agent, or Firm* — McCarter & English, LLP; Beverly W. Lubit

(57) ABSTRACT

The described easy access apparel provides ever day wear that is effective to reduce the stigma of a chronic illness, improve the experience of receiving treatment for a chronic illness, and facilitates access to and utilization of a percutaneous access site.

13 Claims, 9 Drawing Sheets

(56) References Cited

U.S. PATENT DOCUMENTS

| | | | | |
|---|---|---|---|---|
| 6,074,272 | A * | 6/2000 | Hebert | A61F 13/141 450/37 |
| 6,115,840 | A | 9/2000 | Hastings | |
| 6,216,270 | B1 * | 4/2001 | Moquin | A41D 13/1245 2/114 |
| 6,283,124 | B1 * | 9/2001 | Schleuning | A41D 13/1236 128/845 |
| 6,449,815 | B1 | 9/2002 | Spiller | |
| 6,647,552 | B1 * | 11/2003 | Hogan | A41D 13/1245 2/114 |
| 6,694,521 | B1 * | 2/2004 | Hopkins | A41D 13/129 2/114 |
| 7,181,773 | B1 * | 2/2007 | Piraka | A41D 13/1281 2/114 |
| 7,819,911 | B2 * | 10/2010 | Anderson | A61F 7/00 607/107 |
| D655,479 | S | 3/2012 | Umbach et al. | |
| 8,690,835 | B1 * | 4/2014 | Parris | A41D 13/1236 604/174 |
| 8,776,264 | B2 * | 7/2014 | Kiernan | A61B 5/296 2/69 |
| 8,832,864 | B1 * | 9/2014 | Braden | A41D 13/1272 2/114 |
| 8,990,966 | B2 | 3/2015 | Von Furstenberg et al. | |
| D758,697 | S * | 6/2016 | Clark | D2/828 |
| 9,545,124 | B1 * | 1/2017 | Thompson | A41D 13/1281 |
| D816,292 | S * | 5/2018 | Feodoroff | D2/720 |
| 10,092,042 | B2 | 10/2018 | Samuel | |
| D834,787 | S * | 12/2018 | Picot | D2/840 |
| 10,555,568 | B1 * | 2/2020 | Walker-Baldwin | A41B 11/00 |
| D876,753 | S * | 3/2020 | Francis | D2/840 |
| D892,436 | S * | 8/2020 | Francis | D2/750 |
| 10,750,801 | B2 * | 8/2020 | Bentley | A41D 13/1245 |
| 10,945,471 | B1 * | 3/2021 | Reddy | A41D 13/1254 |
| 11,019,860 | B1 * | 6/2021 | Pierce | A41D 13/12 |
| 11,019,861 | B2 * | 6/2021 | Picot | A41D 13/129 |
| 11,116,263 | B2 * | 9/2021 | Czajka | A41D 13/12 |
| 11,202,477 | B1 * | 12/2021 | Dawson | A41D 31/02 |
| 2006/0037124 | A1 * | 2/2006 | Cho | A41D 13/1245 2/114 |
| 2006/0253953 | A1 * | 11/2006 | Williams | A41D 13/1272 2/69 |
| 2007/0083976 | A1 * | 4/2007 | Roy | A41D 13/1236 2/114 |
| 2007/0199127 | A1 * | 8/2007 | Coronado | A41D 13/1254 2/69 |
| 2007/0245450 | A1 * | 10/2007 | Feodoroff | A41D 13/1254 2/114 |
| 2007/0271672 | A1 * | 11/2007 | Lentini | A41D 13/1245 2/69 |
| 2008/0184455 | A1 * | 8/2008 | Blume | A41D 13/1281 2/114 |
| 2008/0282441 | A1 * | 11/2008 | Green | A41D 13/1245 2/69 |
| 2010/0022163 | A1 * | 1/2010 | Widell | A41C 3/10 450/39 |
| 2010/0299803 | A1 * | 12/2010 | Ladra | A41D 13/1254 2/83 |
| 2011/0131701 | A1 * | 6/2011 | Pryne | A41D 13/1245 2/114 |
| 2012/0117710 | A1 * | 5/2012 | Lenzen | A41D 13/1245 2/114 |
| 2013/0067633 | A1 * | 3/2013 | Salem | A41D 13/1245 2/102 |
| 2013/0131566 | A1 * | 5/2013 | Bodansky | A61F 5/37 602/13 |
| 2013/0191977 | A1 * | 8/2013 | Mayeri | A41D 13/1245 2/455 |
| 2014/0026289 | A1 * | 1/2014 | Schulties | A41D 13/1245 2/114 |
| 2014/0157479 | A1 * | 6/2014 | Streep | A41D 13/1236 2/69 |
| 2014/0310850 | A1 * | 10/2014 | Hudak | A41D 13/1245 2/114 |
| 2015/0020288 | A1 * | 1/2015 | Picot | A41D 13/129 2/69 |
| 2015/0067944 | A1 * | 3/2015 | Olson | A41D 13/1236 2/114 |
| 2015/0101102 | A1 * | 4/2015 | Theodossiou | A41D 13/1245 2/114 |
| 2015/0196076 | A1 * | 7/2015 | Billingslea | A41D 13/1245 2/114 |
| 2015/0374048 | A1 * | 12/2015 | Theodossiou | A41D 13/1245 2/114 |
| 2016/0050995 | A1 * | 2/2016 | Bentley | A41D 27/201 2/114 |
| 2016/0095366 | A1 * | 4/2016 | Pruitt | A41D 13/1281 2/114 |
| 2016/0166448 | A1 * | 6/2016 | Laje | A61F 13/0209 604/365 |
| 2016/0286872 | A1 * | 10/2016 | Wilson | A41D 27/10 |
| 2016/0309811 | A1 * | 10/2016 | Tong | A41D 13/1245 |
| 2019/0261707 | A1 * | 8/2019 | Cain | A41D 13/1245 |
| 2020/0013314 | A1 * | 1/2020 | Hare | G09B 23/30 |
| 2020/0214372 | A1 * | 7/2020 | Lindsey | A41D 13/1254 |
| 2020/0397073 | A1 * | 12/2020 | Wolf | A41B 1/18 |
| 2021/0022419 | A1 * | 1/2021 | Carter | A41D 13/1245 |
| 2021/0030078 | A1 * | 2/2021 | House | A41F 9/00 |
| 2021/0100681 | A1 * | 4/2021 | Miles | A41D 13/1254 |
| 2021/0212394 | A1 * | 7/2021 | Wu | A41D 13/1245 |
| 2021/0289855 | A1 * | 9/2021 | Colon-Alfonso | A41D 13/1281 |

OTHER PUBLICATIONS

Schiavon, CC., et al., "Optimism and Hope in Chronic Disease: A Systematic Review." Front Psychol. 2016; 7:2022.

The Joint Commission Preventing Central Line-Associated Bloodstream Infections: Useful Tools, An International Perspective. Nov. 20, 2013. Accessed May 17, 2019. http://www.jointcommission.org/CLABSIToolkit.

www.azuravascularcare.com/infodialysisaccess/dialysis-access-site-functioning/. 10 Tips to Keep Your Dialysis Access Site Functioning, retrieved from internet Dec. 17, 2018.

www.careandwear.com/collections/chest-access-shirts?utm_source=google&utm . . . retrieved from internet Dec. 17, 2018.

www.hemowear.com/blog/benefits-of-easy-access-clothing/. retrieved from internet Dec. 17, 2018.

www.homedialysis.org/life-at-home/helpful-products/clothing. retriveved from internet Dec. 17, 2018.

www.kidney.org/atoz/content/hemoaccess. Hemodialysis Access. National Kidney Foundation, retrieved from internet Dec. 17, 2018.

www.medicalrehabwearinc.com/about-us. Rehab T-Shirts retrieved from internet Dec. 17, 2018.

www.pd-uwear.com/. retriveved from internet Dec. 17, 2018.

* cited by examiner

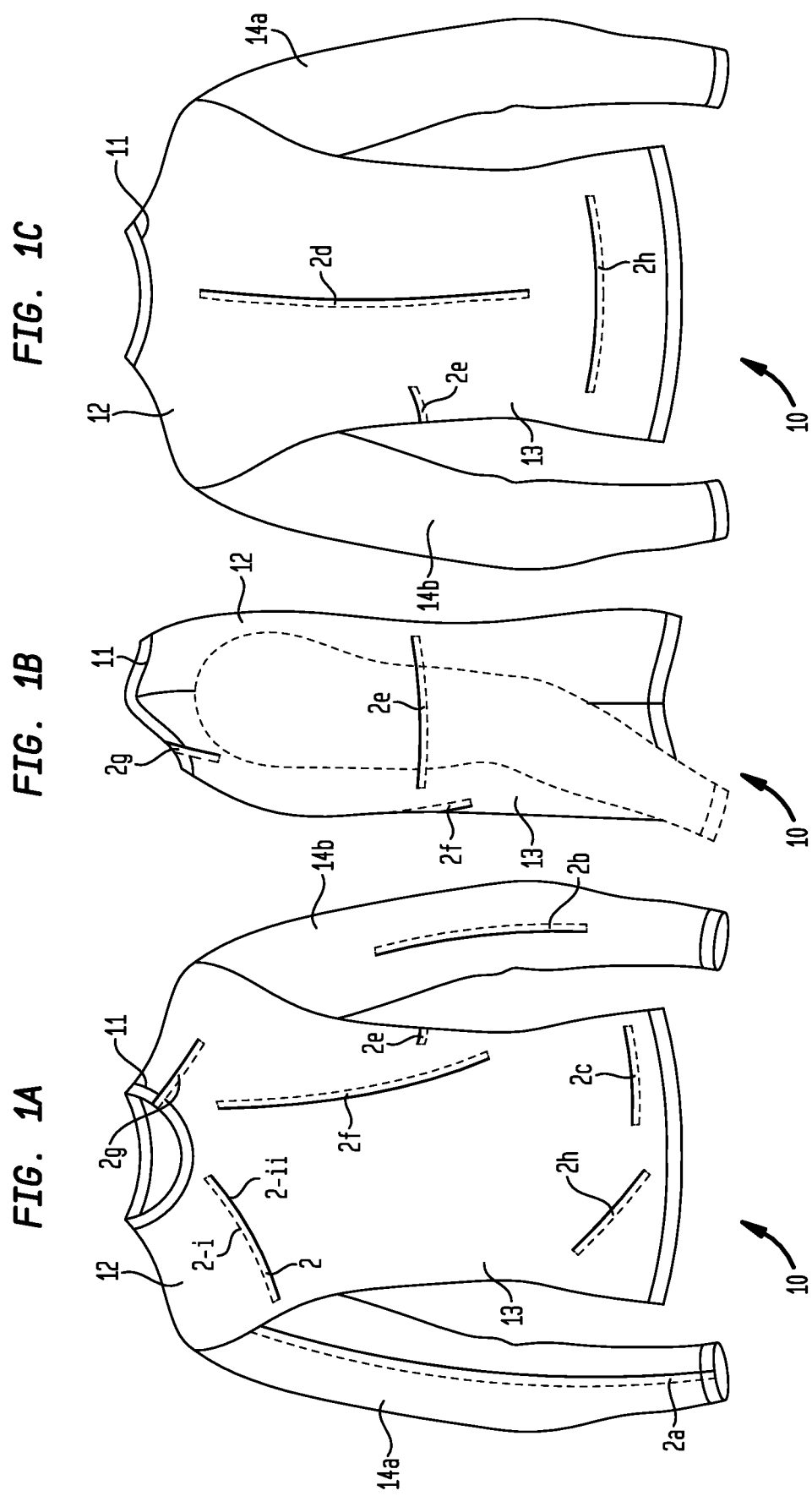

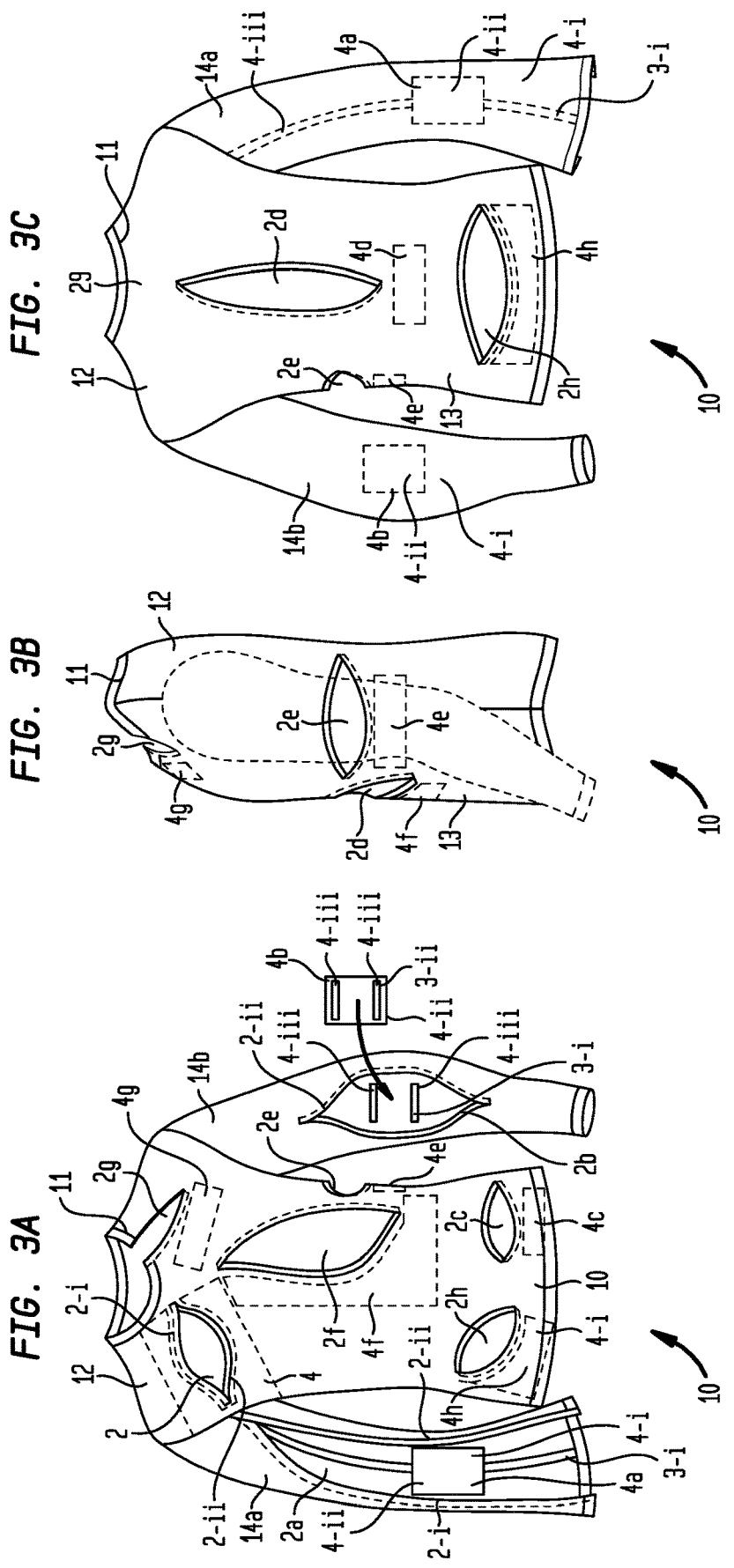

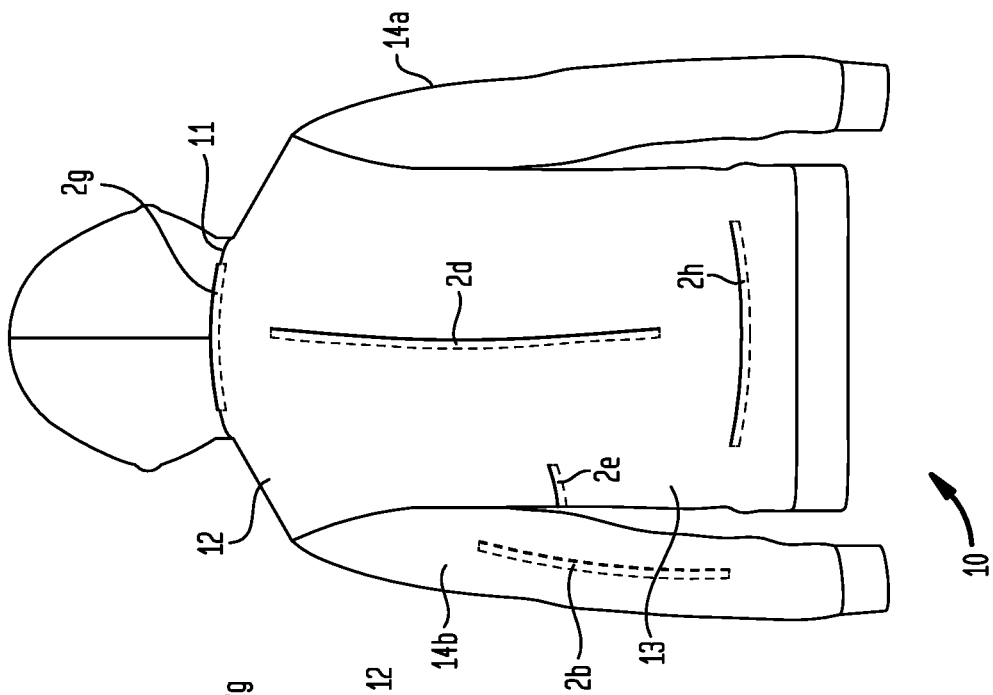
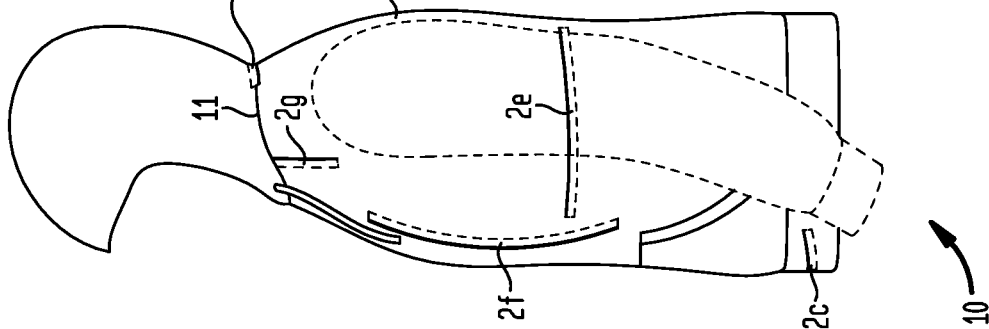
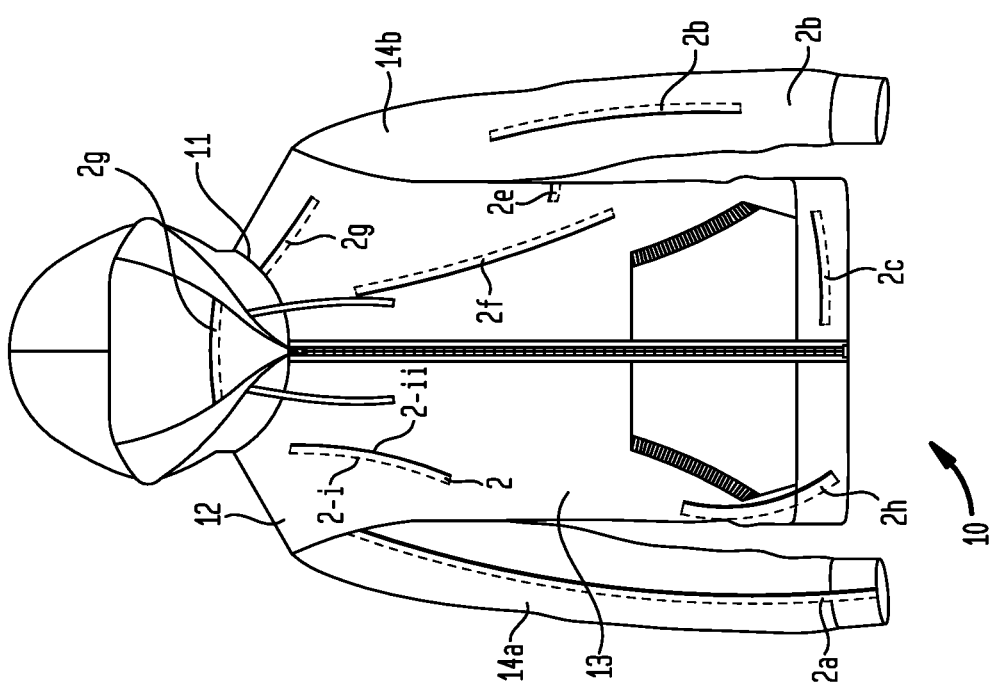

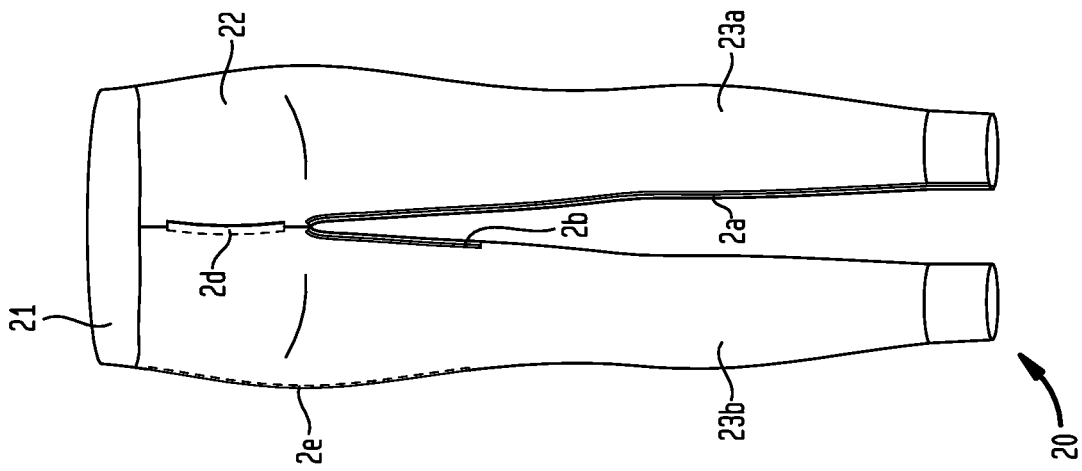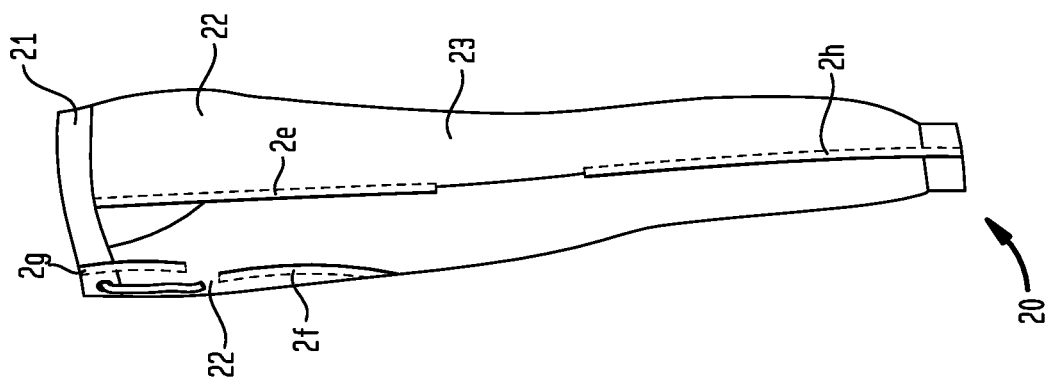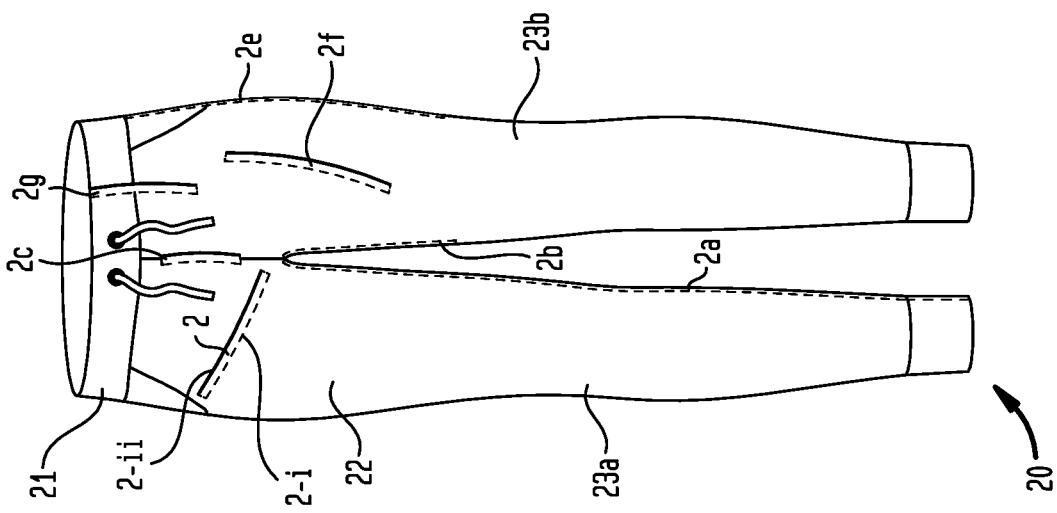

EASY ACCESS APPAREL

RELATED APPLICATION(S)

This application claims the benefit of priority to U.S. Provisional Patent Application No. 62/680,848 filed on Jun. 5, 2018 entitled "MEDICAL SHIRT," the contents of which are incorporated herein by reference in their entirety.

FIELD OF INVENTION

The described invention relates to easy access apparel for comfortable, every day wear by patients having percutaneous access site(s).

BACKGROUND

A percutaneous access site (PAS) is a specific location on a subject's body that acts as a point of access to the inner body spaces and structures for a chronic period of time. A PAS can be characterized by a passage through the skin, a device that is implanted/inserted through the skin, or a device that is synthesized under the skin. A PAS can terminate into any part of the body that needs a point of access, for example the bloodstream, an organ, a region of the nervous system, another implantable device, or a tissue such as adipose, bone, or muscle tissue, and the like.

A percutaneous access site can be used for a number of reasons. For example, it allows the entry, exchange, and/or exit of fluid. In this context, a PAS can be used to deliver medicine, fluids, nutrients, and blood, and can also be used to drain fluid, waste, and/or blood from the body. For example, a PAS can be used to facilitate kidney dialysis such as hemodialysis or peritoneal dialysis. A PAS can further be used to access other implanted devices in the body, such as an artificial organ, or a device that allows for the electrical stimulation of a organ, such as a pacemaker. In this context, a PAS can be used to charge or activate such devices, for example by acting as power supply leads and fluid connections for artificial organs, charging connections for cardiac pacemakers, activation connections for neuroelectric stimulation of nerves and/or muscles, and artificial stimulation and monitoring in various brain implants. A PAS can additionally be used to gather information about biological activity, such as blood flow, or help conduct certain types of medical tests.

The use of a PAS is advantageous in many ways. For instance, it allows continuous and direct access to the body for short-term periods (less than three weeks) and long-term periods (more than three weeks). It can further allow strategic access to the body, for example, a PAS can terminate in a bloodstream that empties near the heart and allows for efficient disbursement of medicine or efficient collection of blood. In another example, by providing direct access to the body, the use of a PAS can avoid degradation of a substance, for example by metabolism through the GI tract. In another example, a PAS can also avoid the discomfort or pain of a subject, namely a patient, being stuck with needles or other foreign objects multiple times.

A PAS can be used in any number of settings, for example, in hospitals, long-term care facilities, outpatient facilities, at a subject's home, and/or for long-term ambulatory care.

There are multiple types of PAS', for instance a PAS can be a foreign object such as a catheter, port, or shunt. A PAS can also be a location on the body where a biological structure is created, such as a fistula, graft, or stoma.

One example of a PAS is an arteriovenous fistula (AV fistula). An AV fistula is created by connecting an artery to a vein, which allows for a high blood flow rate. AV fistulas can be created in any suitable location, such as the arm. AV fistulas can be created, for example, to facilitate hemodialysis.

Another example of a PAS is an arteriovenous graft (AV graft). An AV graft is created by connecting an artery to a vein with a foreign object, such as a tube. An AV graft can be created in any suitable location, such as the arm. The AV graft can be created, for example, to facilitate hemodialysis.

An additional example of a percutaneous access site is a catheter. The term "catheter" as used herein refers to a medical device comprising a thin tube that is inserted into the body for diagnostic or therapeutic reasons. A type of catheter can be a vascular access device (VAD), for example a central venous catheter (CVC). A CVC can be a thin flexible tube that is inserted through the skin and terminates into a blood stream. A CVC can be inserted in any suitable location on the body. For example, a CVC can be inserted in the neck, chest, groin, or arm regions of a subject's body. Some CVCs can terminate into a venous vessel. For example, a CVC can be inserted in a venous great vessel, such as superior vena cava, inferior vena cava, brachiocephalic veins, internal jugular veins, subclavian veins, iliac veins, and common femoral veins. (Rupp et al., "Practice Guidelines for Central Venous Access," Anesthesiology 2012; 116:539-73). Some CVCs can terminate into a systemic artery. There are multiple types of CVCs, such as tunneled, non-tunneled, peripherally inserted, and an implantable type. A subject can have a CVC to deliver medicine, or to exchange fluids. For example, a patient diagnosed with cancer can require a CVC to facilitate chemotherapy treatment. In another example, a patient that requires kidney dialysis can require a CVC to undergo hemodialysis or peritoneal dialysis.

While the use of a PAS can be overall beneficial to a patient, there are several downsides. PAS' are vulnerable to external factors, such as infections or irritation. They are also vulnerable to internal factors such as clotting or scarring. These factors impede the ability of the PAS to function and can also endanger the subject/patient.

Furthermore, many treatment options that include PAS can require downtime in order to undergo treatment. For example, patients undergoing dialysis or chemotherapy can need to stay within reaching distance of their respective machinery often for extended periods of time. Often times, they are in a hospital setting or some other treatment environment that can be sterile, cold, or uncomfortable.

Currently, patients have very limited options of clothing when undergoing such procedures. Original medical clothing worn in the 1800's was based on nightshirts that were popular during that era. Not much has changed today, as most medical garments or gowns used in hospitals and other medical facilities are essentially in the same nightgown shape, with loose ties or snap buttons at the shoulders, sides and/or back to facilitate access to the body of a subject. They generally are made of thin, stiff, and uncomfortable material. While patients can sometimes wear their own clothes in order to be more comfortable, every day clothes are not formed to provide access to the patient's body. Therefore, healthcare providers can ask them to change into hospital wear or otherwise expose themselves as necessary to undergo the procedure. Further, even if patients wear their own clothes to be more comfortable, they run the risk of staining their clothing with body fluids from leakages during procedures.

Typically, patients also find that when a healthcare provider releases the fastenings on the medical garment, the clothing falls away revealing much more of the subject's body than necessary. Such an event can make a patient feel humiliated, mortified, or minimally self-conscious. Many patients report feeling loss of dignity, dehumanization, and stigmatized by looking like a patient; this is likely amplified in patients that require a PAS point, as many patients that obtain a PAS are likely to be seriously ill and/or chronically ill and as such will require extended of periods of time wearing medical clothing.

As discussed supra, patients that obtain a PAS are likely to be seriously ill and/or chronically ill. Research has shown that positive psychological attributes are a significant predictive of positive results for physical health. (Schiavon et al., "Optimism and Hope in Chronic Disease: A Systematic Review." Front Psychol. 2016; 7: 2022). In other words, a patient's mental health can improve their physical health. Factors that can impact a patient's mental health can include quality of life. Patients who are seriously and/or chronically ill can be characterized by requiring long and/or frequent treatment time periods, increased oversight to manage their symptoms, limited mobility, limited diets, and overall a more restrictive lifestyle, which can result in having a low quality of life.

It is important to improve the quality of life for patients who have a chronic or serious illness. One way to improve the quality of life is to improve the experience of obtaining treatment, such as by increasing or maintaining the patient's comfort level during the procedure. For instance, some patients can desire an increase in body temperature in order to maintain or enhance their comfort. In another instance, some patients can desire regulation of their body temperature in order to maintain or enhance their comfort. In another example, some patients can desire a certain amount of modesty to maintain or enhance their comfort. In a further example, some patients can desire a certain amount of dignity to maintain or enhance their comfort. In an additional example, some patients can desire a specific type of environment, such as texture of their clothing, in order to maintain or enhance their comfort.

Therefore, in order to maintain a health PAS, a patient needs a means to be able to comfortably, safely and efficiently access the PAS for treatment, and also for maintenance. The described invention provides everyday clothing that addresses this problem.

SUMMARY OF THE INVENTION

According to one aspect, the describe invention provides an easy access apparel for every day wear by a chronically ill subject who is undergoing chronic medical treatment comprising: a garment comprising (i) at least one closeable opening comprising at least one fastener, and (ii) at least one facilitating member; wherein the at least one closeable opening is effective to facilitate accessibility to a percutaneous access site on the body of a subject; wherein the at least one facilitating member is effective to facilitate utilization of a percutaneous access site on the body of a subject; and wherein the apparel is everyday wear effective to increase the physical, environmental, and emotional comfort of the subject.

According to some embodiments, the garment comprises an inner surface, an outer surface, a right side, a left side, an anterior portion, a posterior portion, a superior end, an inferior end, a lateral end, a medial end, a proximal end, and a distal end.

According to some embodiments, the garment comprises at least one opening formed on the outer surface of the garment through to the inner surface, wherein the at least one opening is formed in the right side, left side, anterior portion, posterior portion, superior end, inferior end, lateral end, medial end, proximal end, and distal end of the garment.

According to some embodiments, the at least one closeable opening further comprises an opening in the garment positioned over a percutaneous access site on the body of subject, a first garment edge and a second garment edge surrounding the opening; and wherein the noncontiguous alignment of the first and second garment edges is effective to open the opening and expose the percutaneous access site, and the contiguous alignment of the first and second garment edges is effective to close the opening and conceal the percutaneous access site.

According to some embodiments, the at least one fastener is a fastening system comprising a first fastening component and second fastening component, wherein the first fastening component is located on the first garment edge and the second fastening component is located on the second garment edge, and the engagement of the first fastening component and the second fastening component results in the closing of the closeable opening, and the disengagement of the first and second fastening components result in the opening of the closeable opening.

According to some embodiments, the fastening system is a flaccid system.

According to some embodiments, the flaccid system is a zipper system.

According to some embodiments, the garment comprises at least one facilitating member positioned on the inner surface of the right side, left side, anterior portion, posterior portion, superior end, inferior end, lateral end, medial end, proximal end, and/or distal end of the garment that facilitates utilization of a percutaneous access site.

According to some embodiments, the facilitating member comprises a facilitating area, facilitating object, and optionally a facilitating attachment component.

According to some embodiments, the facilitating area is an area comprising an outline or border.

According to some embodiments, the facilitating object is an object that limits, prevents or stops fluid leakage during the utilization of a percutaneous access site.

According to some embodiments, the facilitating object is an object that provides anti-microbial, anti-septic, wound healing, and/or protective properties during the utilization of a percutaneous access site.

According to some embodiments, the facilitating object is an object that assists in holding a device in place that is utilizing the percutaneous access site.

According to some embodiments, the facilitating object is an object that functions as a therapeutic or diagnostic device used in conjunction with a device that is utilizing the percutaneous access site.

According to some embodiments, the facilitating object is a sterile disposable absorbent article.

According to some embodiments, the disposable absorbent article comprises one or more selected from the group consisting of flakes, a strip, powders, filaments, fibers, a film, a coating, a textile, a nonwoven material, a napkin, a pad, a mat, a gauze, a dressing, a sponge, a bandage, or a foam.

According to some embodiments, the disposable absorbent article is sterilized gauze.

According to some embodiments, the disposable absorbent article is a sterilized pad.

According to some embodiments, the disposable absorbent article is individually wrapped.

According to some embodiments, the disposable absorbent article comprises one or more layers.

According to some embodiments, the disposable absorbent article comprises a first, second, and third layer, the first layer comprising a liquid permeable material, the second layer comprising a liquid absorbent material, and a third layer comprising a liquid impermeable layer.

According to some embodiments, the liquid permeable materials include textile and non-woven fabric, a perforated film forming polymer, a porous foam, a reticulated foam, a reticulated thermoplastic film or a thermoplastic scrims; the liquid absorbent materials include comminuted wood pulp, creped cellulose cotton, an absorbent foam, an absorbent sponge, a synthetic staple fiber, a polymeric fiber, a hydrogel-forming polymer comprises a gelling agent, or a combination thereof; and the liquid impermeable materials include polyethylene, polypropylene, polyester, a polyamide, ethylene vinyl acetate, polyvinyl chloride, polyvinylidene chloride, cellophane, nitrocellulose or a cellulose acetate film.

According to some embodiments, the disposable absorbent article comprises a fastening system.

According to some embodiments, the fastening system comprises an adhesive.

According to some embodiments, the fastening system comprises a hook fastening component.

According to some embodiments, the fastening system comprises a nylon strap featuring hook and loop fasteners (Velcro®).

According to some embodiments, the garment is a shirt, trousers, or underwear.

According to another aspect, the described invention provides a method of improving comfort of a chronically ill subject who is undergoing chronic medical treatment during utilization of a percutaneous access site comprising providing the subject with easy access apparel for every day wear comprising: a garment comprising (i) at least one closeable opening comprising at least one fastener, and (ii) at least one facilitating member; wherein the at least one closeable opening is effective to facilitate accessibility to a percutaneous access site on the body of a subject; wherein the at least one facilitating member is effective to facilitate utilization of a percutaneous access site on the body of a subject; and wherein the apparel is everyday wear effective to increase the physical, environmental, and emotional comfort of the subject.

According to some embodiments, the easy access apparel is effective to enhance or maintain a subject's perception of dignity.

According to some embodiments, the easy access apparel is effective to enhance or maintain a subject's sensation of modesty.

According to some embodiments, the easy access apparel is effective to enhance or maintain a subject's feeling of normalcy.

These and other advantages of the invention will be apparent to those of ordinary skill in the art by reference to the following detailed description.

BRIEF DESCRIPTION OF DRAWINGS

FIGS. 1A, 1B, 1C are front, side, and back plan views of an embodiment of the Easy Access Apparel of the present invention adapted for use as an Easy Access Shirt showing various positioning of at least one closeable opening(s) where FIG. 1A shows the front view of the Easy Access Shirt, FIG. 1B shows a left or right side view of the Easy Access Shirt, and FIG. 1C shows the back view of the Easy Access Shirt.

FIG. 2A shows the at least one fastener adapted for use as a flaccid system, FIG. 2B shows the at least one fastener adapted for use as a button system, and FIG. 2C shows the at least one fastener adapted for use as a hook-and-loop system.

FIGS. 3A, 3B, 3C are front, side, and back plan views of an embodiment of the Easy Access Apparel of the present invention adapted for use as an Easy Access Shirt showing various positioning of at least one closeable opening(s) and various positioning of at least one facilitating member(s) where FIG. 3A shows the front view of the Easy Access Shirt, FIG. 3B shows a left or right side view of the Easy Access Shirt, and FIG. 3C shows the back view of the Easy Access Shirt.

FIGS. 4A, 4B, 4C are front, side, and back plan views of an embodiment of the Easy Access Apparel of the present invention adapted for use as an Easy Access Shirt showing various positioning of at least one closeable opening(s) where FIG. 4A shows the front view of the Easy Access Shirt, FIG. 4B shows a left or right side view of the Easy Access Shirt, and FIG. 4C shows the back view of the Easy Access Shirt.

FIG. 5A shows the front view of the Easy Access Shirt, FIG. 5B shows a left or right side view of the Easy Access Shirt, and FIG. 5C shows the back view of the Easy Access Shirt.

FIGS. 6A, 6B, 6C are front, side, and back plan views of an embodiment of the Easy Access Apparel of the present invention adapted for use as an Easy Access Trousers showing various positioning of at least one closeable opening(s) where FIG. 6A shows the front view of the Easy Access Trousers, FIG. 6B shows a left or right side view of the Easy Access Trousers, and FIG. 6C shows the back view of the Easy Access Trousers.

FIG. 7A shows the front view of the Easy Access Trousers, FIG. 7B shows a left or right side view of the Easy Access Trousers, and FIG. 7C shows the back view of the Easy Access Trousers.

FIG. 8A shows the front view of the Easy Access Trousers, FIG. 8B shows a left or right side view of the Easy Access Trousers, and FIG. 8C shows the back view of the Easy Access Trousers.

FIG. 9A shows the front view of the Easy Access Underwear, FIG. 9B shows the back view of the Easy Access Underwear, and FIG. 9C shows a left or right side view of the Easy Access Underwear.

DETAILED DESCRIPTION

Definitions

Figure 2A:
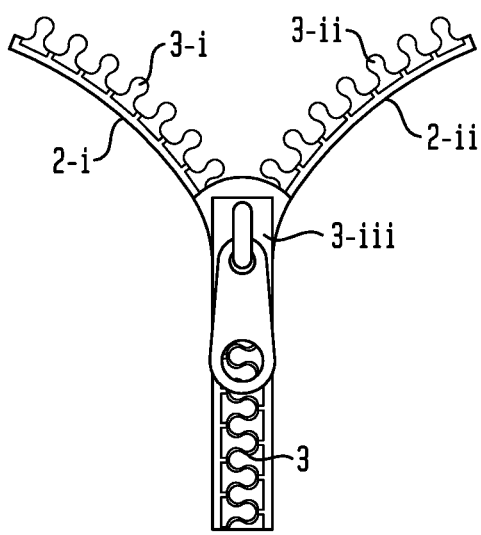
FIGS. 2A, 2B, 2C are top plan views of various embodiments of the at least one fastener of the present invention where

The term "access" as used herein, along with all of its grammatical variations thereof, including but not limited to, "accessed," "accessing," "accesses," "accessible," "accessibility," "accessibleness," "accessibly," "obtain/acquire/attain access to," describes the capability, ability, way, and/or means to enter, approach, reach, and/or contact something; the capability, ability, way, and/or means to pass from one place to another; the state or quality of being approachable, attainable, obtainable, reachable, and/or enterable.

The term "affixed" as used herein is used to describe the state of an object being joined or connected in a non-separable manner with second object. An object can be affixed by any suitable method, such as by machining, casting, molding, stitching, bonding, and/or adhesives.

Anatomical Terms. When referring to humans, the body and its parts are always described using the assumption that the body is standing upright. Portions of the body which are closer to the head end are "superior" (corresponding to the cranial or head end in animals), while those farther away are "inferior." Objects near the front of the body are referred to as "anterior" (corresponding to ventral in animals); those near the rear of the body are referred to as "posterior" (corresponding to dorsal in animals). Structures near the midline, which is the middle of the body, are called medial and those near the sides of humans are called lateral. Structures that are close to the center of the body are "proximal" or central, while ones more distant are "distal" or peripheral. For example, the hands are at the distal end of the arms, while the shoulders are at the proximal ends.

As used herein the term "aperture" describes an open space, hole, slit, crack, gap, passage, breach, or a separation serving as part of a fastener as described herein.

The term "attached" as used herein, along with all of its grammatical variations thereof, including but not limited to "attach," "attachment," "attaching" "attachable," "attachably," is used interchangeably with "engage," "interact," or "penetrate," "interlock," or "mate," to describe the state of an object being fastened, joined, or connected with a second object; or the ability and/or capability of an object being fastened, joined, or connected with a second object; through mechanical, frictional, electrostatic, and/or electromagnetic forces. The term "detached" as used herein, along with all of its grammatical variations thereof, including but not limited to "detach," "detaching," "detachable," "detachably," is used interchangeable with "disengage," "unlock" and "separate," describes the state of an object being unfastened or disconnected from a second object; or the ability and/or capability of an object being unfastened, removed, or disconnected from a second object.

The term "central venous access device" ("CVAD"), is used herein interchangeably with "central venous catheter" ("CVC"), "central access line" ("CAL"), and "central line" ("CL") and describes a device used to access the central venous system for diagnostic or therapeutic reasons.

The ordinary meaning of the term "close" or "closed" refers to the ability, capability, or state of something being put in a position to shut, stop, block, obstruct, make in accessible, hinder access to or passage across, an entrance, gap, passage, aperture, and/or opening; it also means to bring together, join, contact, and/or unite two items. As used herein the term "closable opening" refers to an open space, hole, or a separation formed in a garment that serves as an access point, entry or passage to a percutaneous access site on the body of a subject by exposing the portion of the body where the percutaneous access site is located. The closable opening can be reversibly closed. When a closeable opening is in an opened state, then the percutaneous access site on the body of a subject is exposed. When a closeable opening is in a closed state, then the percutaneous access site on the body of a subject is concealed. A closeable opening is capable of being fully or partially opened/closed depending on the action of the one or more fastener(s) described herein that function(s) to open/close the closeable opening.

The term "comfort" as used herein along with all grammatical variations thereof refers to a contented well-being of a subject. It includes the physical, emotional, and mental state of being of a subject.

As used herein the term "component" is used interchangeably with the terms "element," "part," "thing," "item," or "structure" to describe a constituent of an object.

The ordinary meaning of the term "contact" is the state or condition of touching or being in immediate proximity.

As used herein the term "contiguous," and all grammatical variations thereof, is used to describe two items being in actual contact with one another by touching along a boundary or at a point. As used herein the term "noncontiguous," and all grammatical variations thereof, is used to describe two items that are not in contact with one another.

As used herein, the term "dignity" describes appearance, bearing, conduct or speech indicative of self-respect.

The term "disposable absorbent article" as used herein is used to describe any absorbent material used to dress a lesion or a wound. It can promote healing of the wound/lesion, protect the wound/lesion from further harm, or absorb any fluids that can originate from the wound/lesion or the care thereof. A disposable absorbent article can be formed from any suitable material such as: natural materials, such as cotton, hemp, and the like; synthetic materials, such as, polymers, foam, hydrocolloid, gel, sponges, transparent material; and biologic materials, such as alginate, xenograft, allograft, or autograft, collagen, and the like. A disposable absorbent article can be any suitable size or thickness; and can be any suitable shape, such as circular, ovular, triangular, rectangular, diamond-shaped, crescent shaped, annular, irregular, and the like.

The ordinary meaning of the term "encompass" as used herein means to completely or partially encircle, surround, enclose, and/or envelope something.

As used herein the term "fasten" as used interchangeably with the term "secure," "refasten" and all of the grammatical variations thereof, including but not limited to, "fastening," "securing," "fastened," "secured," "fastenable," and "securable," and is used to describe the attachment of items to each other and/or ability/capability to attach two items to each other. The term "unfasten" as used interchangeably with the term "release" and all grammatical variations thereof, including but not limited to "unfastening," "releasing," "unfastened," and "released," describes the detachment of items from each other and/or the ability/capability to detach items from each other.

As used herein, the term "fastener" describes a device for attaching or connecting two items together in a manner that also allows for the detachment of the two items. The fastener can be readily reusable in that its normal securing and releasing operation is not destructive or damaging to the fastener itself or to the items of which it connects. The fastener comprises fastening components. A "fastening component" is a member, element, thing or part that provides a capability for attaching firmly or fixing securely one item to another item. The term "complementary fastening system" as used herein describes an assembly, assemblage, or combination of complementary "fastening members" or "fastening components" that form a unitary whole, wherein the fastening members attract, interact, engage, or operate cooperatively with each other to accomplish a function, such as to attach two items together by mechanical, frictional, electrostatic, or electromagnetic forces; similarly, the fastening members can interact, disengage, or operate to detach two items. As such, a "male fastening component" has an extension or extended tip, a "female fastening component" has an aperture wherein a male fastening component can be inserted into the female fastening component. An "elongated fastening component" is a fastening component that extends a certain length and works cooperatively with a second elongated fastening component to fasten. An "opposed" fastening component works with a second opposed fastening component that is opposed in its configuration, shape, or character to the first opposed fastening component to fasten.

The ordinary meaning of "form" means to mold, cast, cut, shape, or create something. As used herein, the term "formed in" means something that is formed within an object, but does not require to completely reside within said object. For example, an opening formed in a garment, such as a shirt, and specifically the sleeve of a shirt, can reside completely within the confines of the sleeve or it can extend to the cuff to split the sleeve open or it can extend to the yoke of the shirt. The term "formed by" as used herein refers to methods to mold, cast, cut, shape, or create something. The term "formed of" as used herein refers to the material that is used to mold, cast, cut, shape, or create something. The term "formed on" as used herein refers to the position or location that something is molded, cast, cut, shaped, or created on.

The term "garment" as used herein describes any body covering or clothing that can be used to cover or clothe the body of a subject, includes the terms "apparel," "clothes," "attire," and further encompasses any article of clothing such as blazers, blouse, boxers, bras, briefs, camisoles, cardigans, cargos, chemises, cloaks, coast, corsets, dresses, dressing gowns, gowns, hosiery, jacket, jeans, jumper, kaftan, knickers, nightgowns, nightwear, outerwear, overalls, polos, ponchos, pajamas, robe, romper, saris, sarong, skirts, stockings, sweatshirt, sweater, swimwear, sports wear, socks, suits, tops, T-shirts, trousers, underwear, uniforms, vests, waistcoats, wraps, and the like.

The term "hydrogel" as used herein refers to a substance resulting in a solid, semisolid, pseudoplastic, or plastic structure containing a necessary aqueous component to produce a gelatinous or jelly-like mass.

The phrase "relative to the garment" describes the occurrence that anatomical descriptions will depend on the type of garment. For example, as discussed supra, the terms superior refers to a direction towards the head of a subject. Therefore, in consideration of these terms as applied to a specific type of garment, such as a shirt or trousers, the superior portion of a shirt would be near the collar of a shirt, whereas the superior portion of trousers would be near the waistband of trousers.

The term "modesty" as used herein describes behavior, manner, or appearance intended to avoid impropriety or indecency, by for example, the exposure of skin.

The ordinary meaning of the term "open" refers to the ability, capability or state of something being put in a position to free, clear, unblock, make accessible, make available, allow access to or passage across, an entrance, gap, passage, aperture, and/or opening; it also means to separate, detach, disconnect two items.

The ordinary meaning of the term "position" refers to a condition of something with reference to its place or location.

As used herein, the term "percutaneous," can be used interchangeably with "transcutaneous" or "subcutaneous" to describe a substance or action effected, occurring, or performed through the skin; passing, entering, or penetrating through the skin; and/or occurring, or administered under the skin.

The term "shirt" as used herein describes an article or item of clothing that encompasses a portion of the upper body of a subject and can also be known as a "top." It can originate at the subject's neck and encompass both arms separately. A shirt can be any length and/or size and can be any type of material such as cotton, polyester, denim, wool, leather, silk, blends thereof, and the like. Non-limiting examples of shirts include a camp shirt, dress shirt, dinner shirt, poet shirt, tee or t-shirt, long-sleeve shirt, short sleeve shirt, sleeveless shirt, blouse, camisole, polo shirt, ruby shirt, henley shirt, jersey, baseball shirt, ringer shirt, nightshirt, tunic, onesie or diaper shirt, turtleneck, mockneck, one-shoulder top, halter top, crop top, sleeveless top and the like. A shirt can comprise various parts such as a collar, yoke, bodice, hem, shirt sleeves, shirt cuffs, back pleats, a shirt tail, pockets, fastener(s) and the like.

The terms "subject" or "individual" or "patient" are used interchangeably to refer to a member of an animal species of mammalian origin, including but not limited to, mouse, rat, cat, goat, sheep, horse, hamster, ferret, pig, dog, platypus, guinea pig, rabbit and a primate, such as, for example, a monkey, ape, or human. A human may be of any age, such as infant, pediatric, juvenile, adolescent, adult, or geriatric.

The phrase "subject's perspective" describes the occurrence that anatomical descriptions will depend from the viewpoint of a subject. For example, as discussed supra, the term right side refers to the right-hand side of the subject. Therefore, in consideration of this term as applied to the viewpoint of the subject, the right-hand side would be the side of the body that includes the right hand of the subject.

The term "trousers" as used herein describes an article or item of clothing that encompasses a portion of the lower body of a subject and can also be known as "pants," or "bottoms." It can originate at the subject's waist and encompass both legs separately. Trousers can be any length and size and can be any type of material such as cotton, polyester, denim, wool, corduroy, leather, blends thereof and the like. Non-limiting examples of trousers include bush pants, cargo pants, casual pants, capris, chinos, dress pants, flat front pants, harem pants, hot pants, jeans, jodhpur pants, jumpsuits, khakis, leggings, overalls, palazzos, pleated pants, rompers, skorts, shorts, stirrups, sweat pants, yoga pants, and the like. Trousers can comprise various parts such as a waist band, seat area, crotch area, front rise, trouser or pant-legs, pant cuffs, pockets, a fly, fastener(s), and the like.

The term "underwear" as used herein describes an article or item of clothing that encompasses a portion of the lower body, upper body, or both of a subject. Typically underwear is a type of clothing that is worn under other articles of clothing. Underwear can be any length and size and can be any type of material such as cotton, polyester, wools, and blends thereof, and the like. Non-limiting examples of underwear include a brassiere, sports bras, panties, knockers, briefs, boxer briefs, boxer shorts, camisole, chemise, undershirt, jockstrap, corset, nightwear, petticoats, swimsuits, slips, boyshorts, thongs, long underwear, garters, stockings, hosiery, socks, and the like. Underwear can comprise various parts such as waistband, seat area, crotch area, front rise, leg holes, arm holes, band(s), strap(s), hem, fastener(s) and the like.

As used herein, the term "vascular access device" ("VAD") refers to a device used to access peripheral or central vessels for diagnostic or therapeutic reasons.

Easy Access Apparel

According to some embodiments, the described invention provides an easy access apparel useful for every day use by a patient that can be used to facilitate accessibility utilization of a percutaneous access site (PAS) on a subject. As used herein, PAS describes any site on a subject's body or any device on a subject's body wherein the inner structures of the body can be accessed. According to some embodiments, PAS access can occur during the medical treatment or testing of a subject. According to some embodiments, PAS access can occur during the creation, maintenance, care, and/or cleaning of the PAS.

According to some embodiments, the described invention relates to easy access apparel which can be used to maintain or enhance the comfort of a subject during PAS access. As used herein, maintaining or enhancing comfort is used to describe any physical, environmental or emotional factor, the satisfaction of which promotes a state of well-being. According to some embodiments, the described invention can maintain or enhance physical comfort during PAS access, for example, keeping the subject warm by retaining or increasing the subject's body warmth, or keeping the subject cool by allowing the release of the subject's body heat and/or sweat. According to some embodiments, the described invention can maintain or enhance environmental comfort during PAS access, for example by protecting the subject's skin from the surrounding environment. According to some embodiments, the described invention can maintain or enhance emotional comfort during PAS access, for example by maintaining a subject's modesty, by limiting the area of exposed skin, or by maintaining or increasing subject's dignity, by allowing the patient to feel humanized, normalized, and/or destigmatized.

According to some embodiments, the described invention relates to easy access apparel which can be worn in every day settings outside of the treatment or testing environment. According to some embodiments, the described invention can facilitate or promote the utilization of a PAS. As used herein the facilitating the utilization of a PAS can include the following non-limiting examples: preventing or stopping fluid leakage during the utilization of a PAS; providing anti-microbial, anti-septic, wound healing, and/or protective properties during the utilization of a PAS; assisting in holding a device in place that is accessing a PAS; or by functioning as a therapeutic or diagnostic device used in conjunction with a PAS point.

According to some embodiments, a PAS can be positioned on the right side, left side, anterior, posterior, lateral, medial, superior, and inferior portions of a subject's body.

According to some embodiments, the described invention relates to easy access apparel which has a variety of patient applications, such as, pediatric patients, adult patients, and geriatric patients. According to some embodiments, the described invention relates to easy access apparel which can be worn by a variety of patients, such as, infant, pediatric, juvenile, adolescent, adult, and/or geriatric.

According to some embodiments, the described invention relates to the easy access apparel shown in FIGS. 1A, 1B, 1C, 2A, 2B, 2C, 3A, 3B, 3C, 4A, 4B, 4C, 5A, 5B, 5C, 6A, 6B, 6C, 7A, 7B, 7C, 8A, 8B, 8C, 9A, 9B, and 9C.

According to some embodiments, the easy access apparel comprises
 i. a garment 1;
 ii. at least one closeable opening 2, comprising at least one fastener 3; and
 iii. at least one facilitating member 4.

Garment

According to some embodiments, a garment can be any body covering suitable to encompass a portion of a subject's body. According to some embodiments, the garment 1 can be constructed to encompass a portion of the upper body, lower body, or both of a subject. According to some embodiments, the garment 1 can be any suitable type of garment such as a shirt, trousers, underwear, undershirt, sweater, sweatpants and the like. According to some embodiments, garment 1 can be a shirt. According to some embodiments, garment 1 can be a sweatshirt. According to some embodiments, garment 1 can be an undershirt. According to some embodiments, garment 1 can be trousers. According to some embodiments, garment 1 can be sweatpants. According to some embodiments, garment 1 can be dress pants. According to some embodiments, garment 1 can be underwear.

According to some embodiments, garment 1 comprises a right side and a left side, wherein the right side describes a portion of the garment that encompasses the right-hand side of a subject's body, and the left side describes a portion of the garment that encompasses the left-hand side of a subject's body from the subject's perspective.

According to some embodiments, garment 1 comprises an anterior portion and a posterior portion, wherein the anterior portion describes the portion of the garment that encompasses the anterior portion of a subject's body relative to the garment, and the posterior portion describes the portion of a garment that encompasses the posterior portion of a subject's body relative to the garment.

According to some embodiments, garment 1 comprises a superior portion and an inferior portion, wherein the superior portion describes the portion of the garment that encompasses the superior portion of a subject's body relative to the garment, and the inferior portion describes the portion of a garment that encompasses the inferior portion of a subject's body relative to the garment.

According to some embodiments, garment 1 comprises a lateral portion and a medial portion, wherein the lateral portion describes the portion of the garment that encompasses a lateral portion of a subject's body relative to the garment, and the medial portion describes the portion of a garment that encompasses a medial portion of a subject's body relative to the garment.

According to some embodiments, garment 1 comprises a proximal portion and a distal portion, wherein the proximal portion describes the portion of the garment that encompasses the proximal portion of a subject's body relative to the garment, and the distal portion describes the portion of a garment that encompasses the distal portion of a subject's body relative to the garment.

According to some embodiments, garment 1 can be described as being on the body of a subject when the subject is in a supinated or in a pronated position.

According to some embodiments, garment 1 comprises an inner surface and an outer surface wherein the inner surface faces the skin of the subject and the outer surface faces the external environment.

A garment 1 can be formed by any technique suitable, including without limitation, machining, molding, casting, bonding, stitching, and sewing, and can be formed as a unitary piece or as component pieces attached together by attachment means, such as adhesives, bonding, sewing, or machining.

Garment 1 as a whole or any component thereof can be provided with particular features, such as, being formed with any suitable material/fabric or with additional components; and such as being formed in any suitable shape, length, width, and height.

According to some embodiments, garment 1 can be formed from any suitable material that can maintain or enhance the comfort of a subject during PAS access. As used herein, maintaining or enhancing comfort can be used to describe any physical, environmental or emotional factor, the satisfaction of which promotes a state of well-being. According to some embodiments, garment 1 can be formed from any suitable material that can maintain or enhance physical comfort during PAS access. According to some embodiments, garment 1 can be formed from any suitable material that can maintain or enhance environmental comfort during PAS access. According to some embodiments, garment 1 can be formed from any suitable material that can maintain or enhance emotional comfort during PAS access. Non-limiting examples include soft material, stiff material, light material, thick material, warm material, heat retaining material, heat releasing material, moisture-wicking material, stretch-resistant material, compression material, stretchable material, hydrophobic material, hydrophilic material, water-repellant material, and the like.

According to some embodiments, garment 1 can be formed from any suitable material that can facilitate the utilization of a PAS. For example, garment 1 can be formed from any suitable material that can help increase, facilitate, or direct blood flowrate; limit, prevent, or reduce muscle fatigue; increase oxygenation levels, or provide structure for correct body or musculature positioning, According to some embodiments, garment 1 can be formed with additional components that can facilitate the utilization of a PAS. For example, garment 1 can further comprise a device that senses, monitors, and/or regulates body function of a subject, or the function of the PAS. Non limiting examples include body temperature, respiration rate, blood pressure, blood flow rate, blood count, pulse rate, metabolite level, and the like of a subject.

According to some embodiments, garment 1 can be formed with a dye, design, image, or graphic, by any suitable method, such as by printing, embroidering, texturizing, transferring, ironing, or otherwise machining. According to some embodiments, garment 1 can be formed as single layer or as multiple layers.

Garment 1 can be formed from any type of suitable material, for example: natural materials, such as, cotton, bamboo, flax, jute, silk, hemp, wool, linen, leather, suede, fur, metals, and the like; synthetic materials, such as, elastomers, polymers, polyesters, polyamides, elastic, polyvinyl alcohols, lyocell, vicose, rayon, nylon, acrylic, elastane polyacrylic, mesh and the like; or any combination or blends thereof.

Garment 1 can be manufactured in a variety of sizes to accommodate patients of various ages and body dimensions with the overall formation and individual components substantially proportional for all sizes. For example, garment 1 may be manufactured for an infant subject, pediatric subject, juvenile subject, adolescent subject, adult subject, geriatric subject, plus size subjects, tall subjects, and petite subjects.
Opening According to some embodiments, the opening 2 can be a means for facilitating accessibility to a PAS on the body of a subject. According to some embodiments, opening 2 can be formed by creating an opening from the outer surface of garment 1 through to the inner surface of garment 1 so that the particular area of skin of a subject can be accessed, for example, to access a PAS.

Figure 2B:
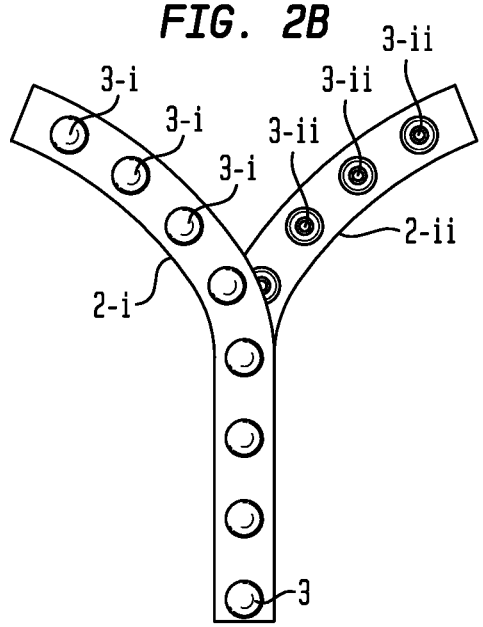
Figure 2C:
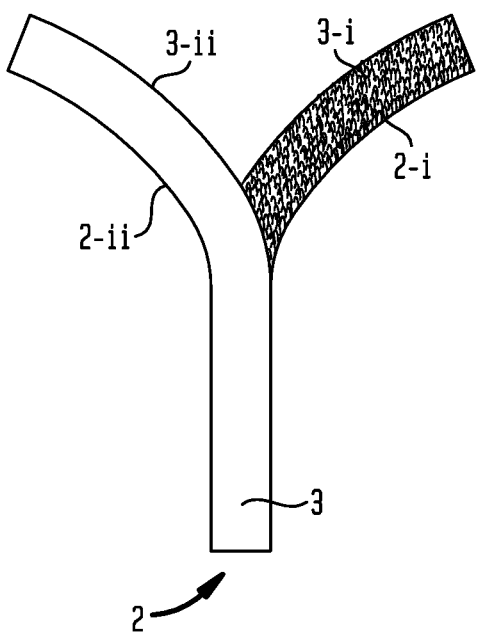

As seen, for example, in FIGS. 2A, 2B, and 2C, according to some embodiments the at least one closeable opening 2 comprises a first edge 2-*i* and a second edge 2-*ii* wherein first edge 2-*i* describes a first edge of the garment 1 and second edge 2-*ii* describes a second edge of garment 1 and opening 2 is the space between the first and second edges.

Opening 2 can be provided with particular features, such as being formed in garment 1 of any suitable shape, length, width and angle. According to some embodiments, the length of opening 2 can be any suitable length, for example 1 inch, 2 inches, 3 inches, 4 inches, 5 inches, 6 inches, 7 inches, 8 inches 9 inches, 10 inches, 11 inches, 1 foot, 2 feet, 3 feet, 4 feet, 5 feet, and the like, and any number in-between. According to some embodiments, when open, the width of opening 2 can be any suitable width, such as, 1 inch, 2 inches, 3 inches, 4 inches, 5 inches, 6 inches, 7 inches, 8 inches 9 inches, 10 inches, 11 inches, 1 foot, 2 feet, 3 feet, 4 feet, 5 feet, 6 feet, the like, inclusive, and any number in-between.

According to some embodiments, the length of opening 2 can be any suitable length relative to the garment or any component of the garment thereof, for example, opening 2 can be a certain length as compared to garment 1, such as $\frac{1}{32}$, $\frac{1}{16}$, $\frac{1}{12}$, $\frac{1}{10}$, $\frac{1}{9}$, $\frac{1}{8}$, $\frac{1}{6}$, $\frac{1}{5}$, $\frac{1}{4}$, $\frac{4}{9}$, $\frac{1}{3}$, $\frac{2}{5}$, $\frac{1}{2}$, $\frac{5}{9}$, $\frac{3}{5}$, $\frac{5}{8}$, $\frac{2}{3}$, $\frac{3}{4}$, $\frac{7}{9}$, $\frac{4}{5}$, $\frac{5}{6}$, $\frac{7}{8}$, $\frac{8}{9}$, or 1/1, the like, inclusive, and any number in-between, of the length of garment 1.

According to some embodiments, when open, the shape of opening 2 can be any suitable shape, such as, circular, ovular, triangular, rectangular, diamond-shaped, crescent shaped, annular, and the like. According to some embodiments, the angle of opening 2 in garment 1 can be any suitable angle, such as an acute, right, obtuse, straight, 15°, 30°, 45°, 60°, 75°, 90°, 105°, 135°, 150°, 180°, 195°, 210°, 225°, 240°, 255°, 270°, 300°, 315°, 330°, 345°, or 360°, the like, inclusive, and any number in-between relative to the superior portion of garment 1.

According to some embodiments, garment 1 comprises at least one opening 2. According to some embodiments, garment 1 comprises at least two openings. According to some embodiments, garment 1 comprises at least three openings. According to some embodiments, garment 1 comprises at least four openings. According to some embodiments, garment 1 comprises at least five openings. According to some embodiments, garment 1 comprises at least six openings. According to some embodiments, garment 1 comprises at least seven openings. According to some embodiments, garment 1 comprises at least eight openings. According to some embodiments, the at least one opening 2 can be formed in any location on garment 1 suitable to facilitate the accessibility to a PAS on the body of a subject.

For example, an opening 2 can be positioned on the inner surface, outer surface, right side, left side, lateral, medial, anterior, posterior, superior and/or inferior portion of garment 1. According to some embodiments, opening 2 can be positioned on the outer surface of garment 1.

According to some embodiments, opening 2 can be positioned on the outer surface of the right side of garment 1. According to some embodiments, opening 2 can be positioned on the outer surface of the left side of garment 1. According to some embodiments, opening 2 can be positioned on the outer surface of the anterior portion of garment 1. According to some embodiments, opening 2 can be positioned on the outer surface of the posterior portion of garment 1. According to some embodiments, opening 2 can be positioned on the outer surface of the lateral portion of garment 1. According to some embodiments, opening 2 can be positioned on the outer surface of the medial portion of garment 1. According to some embodiments, opening 2 can be positioned on the outer surface of the superior portion of garment 1. According to some embodiments, opening 2 can be positioned on the outer surface of the inferior portion of garment 1.

According to some embodiments, the easy access apparel of the described invention can comprise one, two, three, four, five, six, seven, eight, or more openings. According to some embodiments, the easy access apparel can comprise one, two, three, four, five, six, seven, eight or more openings that are positioned in one, two, three, four, five, six, seven, eight or more locations on garment 1. For example, according to some embodiments, opening 2a can be positioned on the outer surface of the right side of garment 1 and opening 2b can be positioned on the outer surface of the left side of garment 1. According to some embodiments, opening 2a can be positioned on the outer surface of the right side of garment 1, opening 2b can be positioned on the outer surface of the left side of garment 1, and opening 2c can be positioned on the outer surface of the anterior portion of garment 1. According to some embodiments, opening 2a can be positioned on the outer surface of the right side of garment 1, opening 2b can be positioned on the outer surface of the left side of garment 1, opening 2c can be positioned on the outer surface of the anterior portion of garment 1, and opening 2d can be positioned on the outer surface of the posterior portion of garment 1. According to some embodiments, opening 2a can be positioned on the outer surface of the right side of garment 1, opening 2b can be positioned on the outer surface of the left side of garment 1, opening 2c can be positioned on the outer surface of the anterior portion of garment 1, opening 2d can be positioned on the outer surface of the posterior portion of garment 1, and opening 2e can be positioned on the outer surface of the lateral portion of garment 1. According to some embodiments, opening 2a can be positioned on the outer surface of the right side of garment 1, opening 2b can be positioned on the outer surface of the left side of garment 1, opening 2c can be positioned on the outer surface of the anterior portion of garment 1, opening 2d can be positioned on the outer surface of the posterior portion of garment 1, opening 2e can be positioned on the outer surface of the lateral portion of garment 1, and opening 2f can be positioned on the outer surface of the medial portion of garment 1. According to some embodiments, opening 2a can be positioned on the outer surface of the right side of garment 1, opening 2b can be positioned on the outer surface of the left side of garment 1, opening 2c can be positioned on the outer surface of the anterior portion of garment 1, opening 2d can be positioned on the outer surface of the posterior portion of garment 1, opening 2e can be positioned on the outer surface of the lateral portion of garment 1, opening 2f can be positioned on the outer surface of the medial portion of garment 1, and opening 2g can be positioned on the outer surface of the superior portion of garment 1. According to some embodiments, opening 2a can be positioned on the outer surface of the right side of garment 1, opening 2b can be positioned on the outer surface of the left side of garment 1, opening 2c can be positioned on the outer surface of the anterior portion of garment 1, opening 2d can be positioned on the outer surface of the posterior portion of garment 1, opening 2e can be positioned on the outer surface of the lateral portion of garment 1, opening 2f can be positioned on the outer surface of the medial portion of garment 1, and opening 2g can be positioned on the outer surface of the superior portion of garment 1 and opening 2h can be positioned on the outer surface of the inferior portion of garment 1.

According to some embodiments, the contiguous alignment of first edge 2-i and a second edge 2-ii thereby closes the closeable opening 2. According to some embodiments, the noncontiguous alignment of first edge 2-i and a second edge 2-ii thereby opens the closeable opening 2.

According to some embodiments, the contiguous alignment of first edge 2-i and a second edge 2-ii closes the closeable opening 2 thereby concealing a PAS on the body of a subject. According to some embodiments, the noncontiguous alignment of first edge 2-i and second edge 2-ii opens the closeable opening 2 thereby exposing a PAS on the body of a subject.

An opening 2 can be formed by any technique suitable, such as by machining, molding, casting, bonding, cutting, sewing or stitching, and can be formed during the manufacturing process of the garment 1 or formed after the manufacturing process of the garment 1 and later affixed.

Fastener

According to some embodiments, the fastening of the at least one fastener 3 can result in the closing of the closeable opening 2. According to some embodiments, the unfastening of the least one fastening 3 can result in the opening of the closeable opening 2.

According to some embodiments, the securing of the at least one fastener 3 can result in the contiguous alignment of a first edge 2-i and a second edge 2-ii thereby closing the closeable opening 2. According to some embodiments, the releasing of the at least one fastener 3 can result in the noncontiguous alignment of first edge 2-i and second edge 2-ii thereby opening the closeable opening 2.

According to some embodiments, the at least one fastener 3 can be released to open the at least one opening 2 thereby exposing a PAS on the body of a subject. According to some embodiments, the at least one fastener 3 can be secured to close the at least one opening 2 thereby concealing a PAS on the body of a subject.

According to some embodiments, the at least one fastener 3 can be formed in any location on the closeable opening 2 effective to open and close the closeable opening 2 and/or to contiguously and noncontiguously align first edge 2-i and second edge 2-ii. According to some embodiments, the at least one fastening 3 can be formed on first edge 2-i and/or second edge 2-ii. According to some embodiments, the at least one fastening 3 can be formed on the outer surface of first edge 2-i and/or second edge 2-ii. According to some embodiments, the at least one fastening 3 can be formed the inner surface of first edge 2-i and/or second edge 2-ii.

According to some embodiments, opening 2 comprises any number of fastener 3 necessary or sufficient to open and close opening 2 and/or to contiguously and noncontiguously align first edge 2-i and second edge 2-ii. According to some embodiments, opening 2 comprises at least two fasteners. According to some embodiments, opening 2 comprises at least three fasteners. According to some embodiments, opening 2 comprises at least four fasteners. According to some embodiments, opening 2 comprises at least five fasteners. According to some embodiments, opening 2 comprises at least six fasteners. According to some embodiments, opening 2 comprises at least seven fasteners. According to some embodiments, opening 2 comprises at least eight fasteners.

According to some embodiments, opening 2 comprises at least nine fasteners. According to some embodiments, opening 2 comprises at least ten fasteners.

Fastening system. According to some embodiments, the at least one fastener 3 can be any suitable type of complementary fastening system comprising a fastening component.

According to some embodiments, the complementary fastening system comprises a first fastening component and a second fastening component wherein the interaction of the first and second fastening components can result in the opening or the closing of the opening 2.

According to some embodiments, the first fastening component can be positioned on the first opening edge 2-i, and the second fastening component can be positioned on the second opening edge 2-ii. According to some embodiments, the engagement of the first and second fastening components can result in the contiguous alignment of opening edges 2-i and 2-ii thereby closing the opening 2. According to some embodiments, the disengagement of the first and second fastening components can result in the noncontiguous alignment of the opening edges 2-i and 2-ii thereby opening the opening 2.

According to some embodiments, the at least one fastener 3 comprises any suitable type of complementary fastening system comprising a first fastening component 3-i on first opening edge 2-i and a second fastening component 3-ii on second opening edge 2-ii. According to some embodiments, fastening components 3-i and 3-ii can be any suitable fastening component such as a male, female, opposed, and/or elongated fastening component. According to some embodiments the fastening system further comprises a third fastening component 3-iii which can facilitate the fastening of opening edges 2-i and 2-ii.

Exemplary complementary fastening systems can include, but are not limited to, a button system, a slide system, a buckle system, a pin system, a flaccid system, or a hook-and-loop system.

According to some embodiments, a button system comprises a rigid or semirigid male component, such as a button or a pin, which can be attached to the portion of the surface of the structure to which it can be intended to fasten, and a complementary flaccid female aperture component, such as a buttonhole or a pinhole which can be positioned on the opposing surface of the intended structure, whereby the mating of the male component through the female component, such as by penetrating the female component with the male component, thereby results in the fastening of the structure; and whereby the removal of the male component from the female component thereby results in the unfastening of the structure.

For example, if the complementary fastening system is a button system as seen in FIG. 2B, according to some embodiments the at least one opening 2 comprises a first edge 2-i and a second edge 2-ii; wherein first edge 2-i and a second edge 2-ii overlap so that the outer surface of the first edge 2-i can come in contact with the inner surface of the second edge 2-ii; a rigid male component 3-i attached to the outer surface of the first edge 2-i and a flaccid female component 3-ii formed in the second edge 2-ii; whereby the mating of the male component on the outer surface of 2-i through the female component from the inner surface of the second edge 2-ii thereby resulting in the contiguous alignment of edges 2-i and 2-ii, and the fastening of the opening 2; whereby the removal of the male component 3-i from the female component 3-ii thereby results in the noncontiguous alignment of edges 2-i and 2-ii, and the unfastening of the opening 2.

According to some embodiments, the male component of a button system can be a button and the female component can be a buttonhole. According to some embodiments, the male component of a button system can be a pin and the female component can be a pinhole.

According to some embodiments, a slide system comprises a first elongated fastening component and a second elongated fastening component on opposing structures, and a sliding device; wherein the first and second elongated fastening components are configured to interlockingly engage with each other; and wherein the sliding device can travel along the length of the first and second fastening components to force them to be interlockingly engaged thereby resulting in fastening of the structure; and wherein the sliding device can travel in the opposite direction of the length of the interlocked first and second fastening components to force them to disengage thereby resulting in the unfastening in the structure.

For example, if the complementary fastening system is a slide system as seen in FIG. 2A, according to some embodiments the at least one opening 2 comprises a first edge 2-i and a second edge 2-ii that are parallel; a first elongated component 3-i attached to the first edge 2-i, a second elongated component 3-ii attached to the second edge 2-ii; and a sliding device 3-iii; wherein the first and second elongated fastening components 3-i and 3-ii are configured to interlockingly engage with each other; and wherein sliding device 3-iii travels along the length of the first and second fastening components 3-i and 3-ii to force them to be interlockingly engaged thereby resulting in the contiguous alignment of edges 2-i and 2-ii, and the fastening of opening 2; and wherein sliding device can travel in the opposite direction of the length of the interlocked first and second fastening components 3-i and 3-ii to force them to disengage thereby resulting in the noncontiguous alignment of edges 2-i and 2-ii, and the unfastening of opening 2.

According to some embodiments, the first and second elongated components of a slide system can be zipper tape and the sliding device can be a zipper slider.

According to some embodiments, a hook-and-loop system comprises a hook male fastening component, affixed to the surface of the structure intended to be fastened, and a loop female fastening component, affixed to an opposing surface of the intended structure, whereby the antiparallel engagement of the hook component and the loop component results in the fastening of the structure; and whereby the disengagement of the hook and loop components thereby results in the unfastening of the structure.

For example, if the complementary fastening system is a hook-and-loop system as seen in FIG. 2C, according to some embodiments the at least one opening 2 comprises a first edge 2-i and a second edge 2-ii; wherein first edge 2-i and a second edge 2-ii overlap so that the outer surface of the first edge 2-i can come in contact with the inner surface of the second edge 2-ii; a hook male component 3-i affixed to the outer surface of first edge 2-i and a loop female component 3-ii affixed to second edge 2-ii; whereby antiparallel engagement of the hook component 3-I and loop component 3-ii results in the contiguous alignment of edges 2-i and 2-ii, and the fastening of the opening 2; whereby the disengagement of hook component 3-i from loop component 3-ii thereby results in the noncontiguous alignment of edges 2-i and 2-ii, and the unfastening of the opening 2.

According to some embodiments, types of hook-and-loop systems include, but are not limited to, a nylon strap featuring hook and loop fasteners (Velcro®), or hook-and-eyelet.

Fastener 3 can also be described in any other component of the described invention in that at least one fastener 3 can be used on any other location on easy access apparel, including for example on a location on garment 1 that is not opening 2, and/or on facilitating member 4.

A fastener 3 can be formed by any technique suitable, such as, by molding, casting, machining, bonding, sewing or stitching, and can be formed during the manufacturing process of the easy access apparel or can be formed as a separate part and can be later affixed.

Fastener 3 can be made from any type of suitable material. Exemplary materials include, but are not limited to: natural materials, such as, metal, wood, and cloth; chemical materials, such as, adhesives; and polymer materials, such as, plastic, rubber, elastic, latex, silicone, nylon, polyester, and vinyl. The fastener 2 can be attached to the opening 2 by any attachment means suitable such as adhesives, bonding, sewing, or machining.

Facilitating Member

According to some embodiments, a means for facilitating the use of a PAS on the body of a subject can be the at least one facilitating member 4. According to some embodiments, a means for facilitating the use of a PAS on the body of a subject can include a means, for example, for preventing or stopping fluid leakage during the utilization of a PAS; providing anti-microbial, anti-septic, wound healing, and/or protective properties during the utilization of a PAS; assisting in holding a device in place that is accessing a PAS, or by functioning as a therapeutic or diagnostic device used in conjunction with a PAS point.

According to some embodiments, the facilitating member 4 once positioned is not unduly bulky, awkwardly large, big or clumsy. According to some embodiments, the facilitating member once positioned is instead sleek, compact and manageable.

According to some embodiments, the at least one facilitating member 4 can be in any location on garment 1 suitable to facilitate the use of a PAS. For example, a facilitating member 4 can be positioned on the inner surface, outer surface, right side, left side, lateral, medial, anterior, posterior, superior and/or or inferior portion of garment 1. According to some embodiments, facilitating member 4 can be positioned on the inner surface of garment 1. According to some embodiments, facilitating member 4 can be positioned on the inner surface of the right side of garment 1. According to some embodiments, facilitating member 4 can be positioned on the inner surface of the left side of garment 1. According to some embodiments, facilitating member 4 can be positioned on the inner surface of the anterior portion of garment 1. According to some embodiments, facilitating member 4 can be positioned on the inner surface of the posterior portion of garment 1. According to some embodiments, facilitating member 4 can be positioned on the inner surface of the lateral portion of garment 1. According to some embodiments, facilitating member 4 can be positioned on the inner surface of the medial portion of garment 1. According to some embodiments, facilitating member 4 can be positioned on the inner surface of the superior portion of garment 1. According to some embodiments, facilitating member 4 can be positioned on the inner surface of the inferior portion of garment 1.

Facilitating member 4 can be provided with particular features, such as being formed of a suitable shape, length, width, area and angle on garment 1.

According to some embodiments, the easy access apparel of the described invention can comprise one, two, three, four, five, six, seven, eight, or more facilitating members.

According to some embodiments, easy access apparel can comprise one, two, three, four, five, six, seven, eight or more facilitating members that are positioned in one, two, three, four, five, six, seven, eight or more locations on garment 1.

For example, according to some embodiments, facilitating member 4a can be positioned on the inner surface of the right side of garment 1 and facilitating member 4b can be positioned on the inner surface of the left side of garment 1. According to some embodiments, facilitating member 4a can be positioned on the inner surface of the right side of garment 1, facilitating member 4b can be positioned on the inner surface of the left side of garment 1, and facilitating member 4c can be positioned on the inner surface of the anterior portion of garment 1. According to some embodiments, facilitating member 4a can be positioned on the inner surface of the right side of garment 1, facilitating member 4b can be positioned on the inner surface of the left side of garment 1, facilitating member 4c can be positioned on the inner surface of the anterior portion of garment 1, and facilitating member 4d can be positioned on the inner surface of the posterior portion of garment 1. According to some embodiments, facilitating member 4a can be positioned on the inner surface of the right side of garment 1, facilitating member 4b can be positioned on the inner surface of the left side of garment 1, facilitating member 4c can be positioned on the inner surface of the anterior portion of garment 1, facilitating member 4d can be positioned on the inner surface of the posterior portion of garment 1, and facilitating member 4e can be positioned on the inner surface of the lateral portion of garment 1. According to some embodiments, facilitating member 4a can be positioned on the inner surface of the right side of garment 1, facilitating member 4b can be positioned on the inner surface of the left side of garment 1, facilitating member 4c can be positioned on the inner surface of the anterior portion of garment 1, facilitating member 4d can be positioned on the inner surface of the posterior portion of garment 1, facilitating member 4e can be positioned on the inner surface of the lateral portion of garment 1, and facilitating member 4f can be positioned on the inner surface of the medial portion of garment 1. According to some embodiments, facilitating member 4a can be positioned on the inner surface of the right side of garment 1, facilitating member 4b can be positioned on the inner surface of the left side of garment 1, facilitating member 4c can be positioned on the inner surface of the anterior portion of garment 1, facilitating member 4d can be positioned on the inner surface of the posterior portion of garment 1, facilitating member 4e can be positioned on the inner surface of the lateral portion of garment 1, facilitating member 4f can be positioned on the inner surface of the medial portion of garment 1, and facilitating member 4g can be positioned on the inner surface of the superior portion of garment 1. According to some embodiments, facilitating member 4a can be positioned on the inner surface of the right side of garment 1, facilitating member 4b can be positioned on the inner surface of the left side of garment 1, facilitating member 4c can be positioned on the inner surface of the anterior portion of garment 1, facilitating member 4d can be positioned on the inner surface of the posterior portion of garment 1, facilitating member 4e can be positioned on the inner surface of the lateral portion of garment 1, facilitating member 4f can be positioned on the inner surface of the medial portion of garment 1, and facilitating member 4g can be positioned on the inner surface of the superior portion of garment 1 and facilitating member 4h can be positioned on the inner surface of the inferior portion of garment 1.

According to some embodiments, the length of facilitating member 4 can be any suitable length, for example 0.001 inch, 0.01 inch, 0.1 inch, 1 inch, 2 inches, 3 inches, 4 inches, 5 inches, 6 inches, 7 inches, 8 inches 9 inches, 10 inches, 11 inches, 1 foot, 2 feet, 3 feet, 4 feet, 5 feet, and the like, and any number in-between.

According to some embodiments, the width of facilitating member 4 can be any suitable width, such as, 0.001 inch, 0.01 inch, 0.1 inch, 1 inch, 2 inches, 3 inches, 4 inches, 5 inches, 6 inches, 7 inches, 8 inches 9 inches, 10 inches, 11 inches, 1 foot, 2 feet, 3 feet, and the like, and any number in-between.

According to some embodiments, the area of facilitating member 4 can be any suitable area, such as, 0.000001 square inch, 0.0001 square inch, 0.001 square inch, 0.01 square inch, 0.1 square inch, 1 square inch, 2 square inch, 3 square inches, 4 square inches, 5 square inches, 6 square inches, 7 square inches, 8 square inches, 9 square inches, 10 square inches, 11 square inches, 12 square inches, and the like, and any number in-between.

According to some embodiments, the shape of facilitating member 4 can be any suitable shape, such as, circular, ovular, triangular, rectangular, diamond-shaped, crescent shaped, annular, irregular, and the like.

According to some embodiments, the angle of facilitating member 4 on garment 1 can be any suitable angle, such as an acute, right, obtuse, straight, 15°, 30°, 45°, 60°, 75°, 90°, 105°, 135°, 150°, 180°, 195°, 210°, 225°, 240°, 255°, 270°, 300°, 315°, 330°, 345°, or 360° relative to the superior portion of garment 1.

Facilitating member 4 can be formed by any technique suitable, such as, by sewing or machining, and can be formed during the manufacturing process of the easy access apparel or can be formed as a separate part and can be later affixed to garment 1.

Facilitating member 4 can be any means that facilitates the use of a PAS, for example, it can be a designated area on the garment, a foreign object, or a means to attach a foreign object, or any combination thereof. According to some embodiments, facilitating member 4 comprises an area formed on garment 1 that facilitates the use of a PAS. According to some embodiments, facilitating member 4 comprises an object that facilitates the use of a PAS. According to some embodiments, the facilitating member 4 comprises a means to attach an object that facilitates the use of a PAS. According to some embodiments, facilitating member 4 comprises an area formed on garment 1 and an object that facilitate the use of a PAS. According to some embodiments, facilitating member 4 comprises an area formed on garment 1, an object positioned on garment 1, and a means to attach an object that facilitates the use of a PAS.

Facilitating Area. According to some embodiments, facilitating member 4 comprises an area formed on garment 1 that facilitates the use of a PAS. As used herein, an area that facilitates the use of a PAS can be referred to as a facilitating area 4-i.

According to some embodiments, facilitate area 4-i can be formed of the same material as garment 1. According to some embodiments, facilitating area 4-i can be formed from a material that is different than garment 1. According to some embodiments, facilitating area 4-i can be formed by an outline or border. According to some embodiments, facilitating area 4-i can be formed of a specific type of texture, material, coating or coatings, treatment or treatment, layer or layers that facilitate the utilization of a PAS by preventing or stopping fluid leakage during the utilization of a PAS; providing anti-microbial, anti-septic, wound healing, and/or protective properties during the utilization of a PAS; assisting in holding a device in place that is accessing a PAS, or by functioning as a therapeutic or diagnostic device used in conjunction with a PAS point.

Facilitating Object. According to some embodiments, facilitating member 4 comprises an object that facilitates the use of a PAS. As used herein, an object that facilitates the use of a PAS can be referred to as a facilitating object 4-ii.

According to some embodiments, facilitating object 4-i can be attached to garment 1 by attachment means. According to some embodiments, facilitating object 4-ii is attached to garment 1 or facilitating area 4-i by any means suitable, for example by affixment methods such as adhesives, bonding, stitching, sewing or adhesives; by fastening methods such as by at least one fastener 3; by manual application methods, such as by spraying, painting, coating, treating, and the like.

According to some embodiments, the facilitating object 4-i is sterile, or substantially free from microbial contamination such as bacteria, fungi, and/or viral contamination. According to some embodiments, the facilitating object is adapted to be sterilized. The facilitating object can be sterilized by any suitable means, including but not limited to, treatment with one or more antimicrobial solutions, processing in an autoclave, irradiation by gamma rays, irradiation by UV rays, and etc. According to some embodiments, the facilitating object 4-ii is individually wrapped.

According to some embodiments, a facilitating object 4-ii can be used to, for example, limit, prevent or stop fluid leakage. According to some embodiments, a facilitating object 4-ii that limits, prevents, or stops fluid leakage can be a disposable absorbent article. According to some embodiments, the disposable absorbent article can be formed of any suitable material. According to some embodiments, the facilitating object is readily accessed for one or more of positioning, removal, or replacement as needed. Non limiting examples include: flakes, strips, powders, filaments, fibers; a thin layer of material such as a film, coating, treatment; textiles, nonwoven materials; napkins, pads, mats, gauze, dressings, sponges, bandages, foam; blends and/or layers thereof.

According to some embodiments, the disposable absorbent article can be formed of any suitable materials. Non-limiting exemplary materials include: textile and non-woven fabric, a perforated film forming polymer, porous foams, reticulated foams, reticulated thermoplastic films, thermoplastic scrims, comminuted wood pulp, creped cellulose cotton, absorbent foams, absorbent sponges, synthetic staple fibers, polymeric fibers, a hydrogel-forming polymer comprising a gelling agent; polyethylene, polypropylene, polyesters, polyamides, ethylene vinyl acetate, polyvinyl chloride, polyvinylidene chloride, cellophane, nitrocellulose, cellulose acetate, equivalents thereof, a combination of these materials, and/or layers thereof.

According to some embodiments, the disposable absorbent article can be formed of one layer or more than one layer. For example, the disposable absorbent article can comprise a first, second, and third layer, the first layer comprising a liquid permeable material, the second layer comprising a liquid absorbent material, and a third layer comprising a liquid impermeable layer. Nonlimiting examples of liquid permeable materials include textile and non-woven fabric, a perforated film forming polymer, porous foams, reticulated foams, reticulated thermoplastic films and thermoplastic scrims. Nonlimiting examples of liquid absorbent materials include comminuted wood pulp, creped cellulose cotton, absorbent foams, absorbent sponges, synthetic staple fibers, polymeric fibers, a hydrogel-forming polymer comprises a gelling agent, such as a chain or network of hydrophilic monomers, or equivalents thereof or a combination of these materials. Nonlimiting examples of liquid impermeable materials include polyethylene, polypropylene, polyesters, polyamides, ethylene vinyl acetate, polyvinyl chloride, polyvinylidene chloride, cellophane, nitrocellulose and cellulose acetate film.

According to some embodiments, facilitating object 4-*ii* can be used to, for example, hold a device in place that is accessing a PAS. According to some embodiments, facilitating object 4-*ii* can be a fastening component, such as a clamp, corded elastic, magnets, and the like.

According to some embodiments, facilitating object 4-*ii* can be used to, for example, function as a therapeutic or diagnostic device that is used in conjunction with a PAS point. According to some embodiments, facilitating object can be a device that senses, monitors, and/or regulates body function of a subject, or the function of the PAS, such as a thermometer, heart-rate monitor, blood-pressure monitor, and the like.

According to some embodiments, facilitating object 4-*ii* can be provided with particular features, such as being formed with anti-microbial (such as, antibacterial, antiviral, antifungal, and the like) anti-septic, wound healing, protective properties, and the like. According to some embodiments, facilitating object 4-*ii* can be formed from or treated with an anti-microbial substance, anti-septic substance, wound-healing substance, or a substance with protective properties.

Facilitating means. According to some embodiments, the facilitating member 4 comprises a means to attach an object that facilitates the use of a PAS. As used herein, attachment means that facilitates the use of a PAS can be referred to as a facilitating means 4-*iii*. According to some embodiments, the facilitating member comprises any facilitating means 4-*iii* suitable to attach facilitating object 4-*ii* to garment 1 or to facilitating area 4-*i*.

According to some embodiments, facilitating means 4-*iii* comprises a panel, sleeve, pocket, cavity, pouch, binding, or the like that allows the facilitating object 4-*ii* to be inserted into the panel, sleeve, pocket, cavity, pouch, or binding, thereby resulting in the attachment of facilitating object 4-*ii* to garment 1.

According to some embodiments, facilitating means 4-*iii* comprises a fastener 3 to mechanically, frictionally, electrostatically, or electromagnetically attach a facilitating object 4-*ii* to garment 1. According to some embodiments, facilitating member fastener 3 comprises a fastening system wherein garment 1 contains a first fastening component 3-*i* and facilitating object contains a second fastening component 3-*ii* so that the interaction of the first component and the second component can result in the fastening of the facilitating object to garment 1. For example, facilitating member comprises a fastener 3 which can be a hook-and-loop fastening system, wherein garment 1 contains the hook component 3-*i* and the facilitating object contains the loop component 3-*ii* so that the engagement of the hook and loop components can result in the fastening of the facilitating object to garment 1.

According to some embodiments, facilitating means 4-*iii* can attach facilitating object 4-*ii* to garment 1 or to facilitating area 4-*i* by any means suitable, for example by affixment methods such as adhesives, bonding, stitching, sewing or adhesives; by fastening methods such as by at least one fastener 3; by manual application methods, such as by spraying, painting, coating, treating, and the like.

Easy Access Shirt

As seen in FIGS. 1A, 1B, 1C, 2A, 2B, 2C, 3A, 3B, 3C, 4A, 4B, 4C, 5A, 5B, and 5C, according to some embodiments, the garment 1 is a shirt 10 wherein the easy access apparel comprises i. a shirt 10;

ii. at least one closeable opening 2, comprising at least one fastener 3; and iii. at least one facilitating member 4.

Figure 5A:
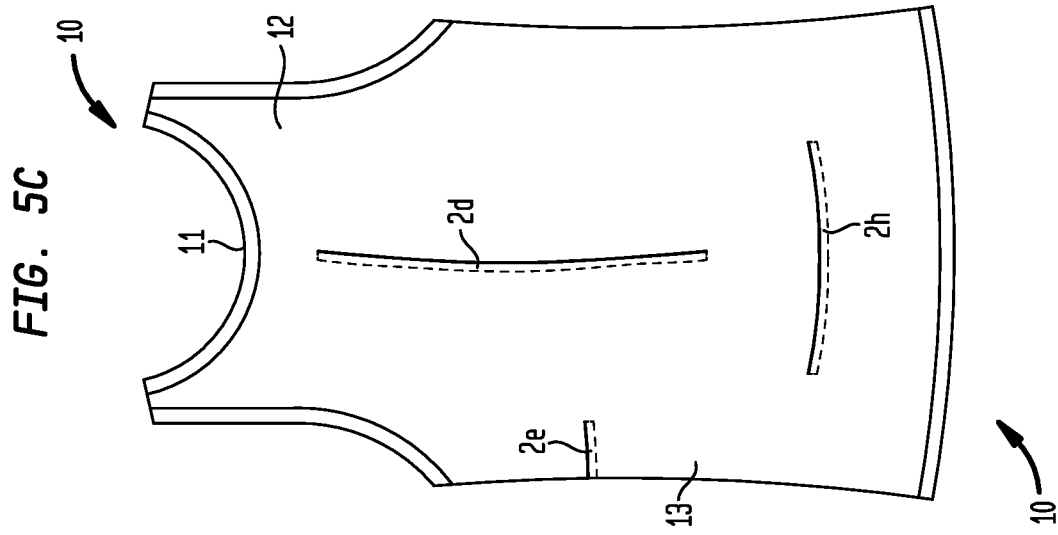
FIGS. 5A, 5B, 5C are front, side, and back plan views of an embodiment of the Easy Access Apparel of the present invention adapted for use as an Easy Access Shirt showing various positioning of at least one closeable opening(s) where
Figure 5B:
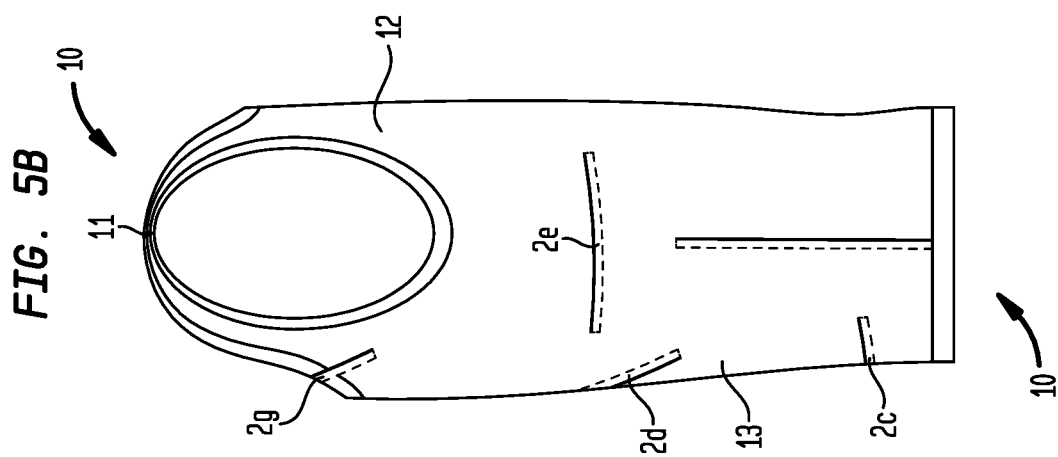
Figure 5C:
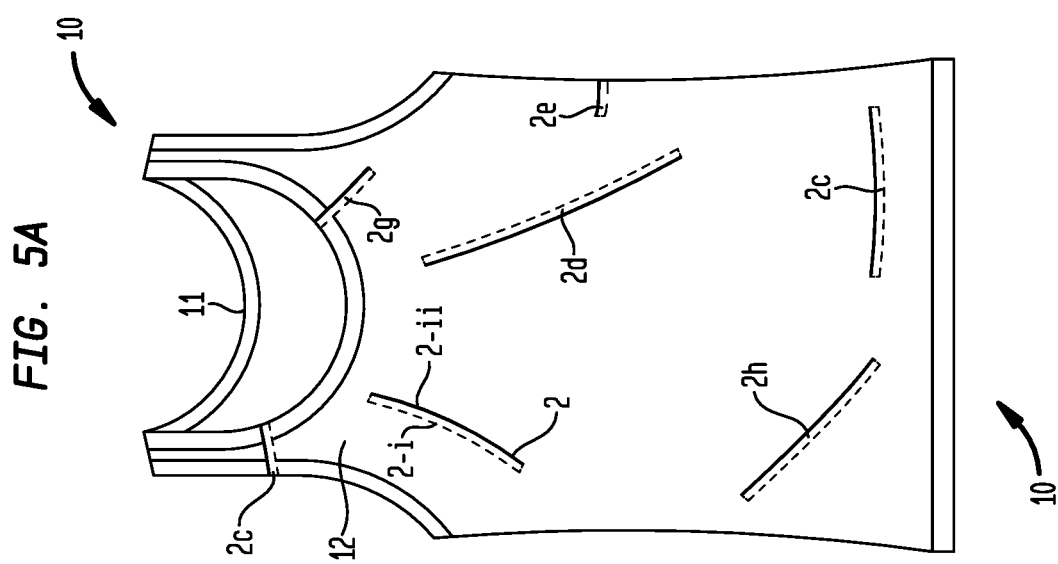

According to some embodiments, shirt 10 is any shirt that is constructed to encompass the upper body of a subject. According to some embodiments, shirt 10 can be any type of shirt such as a casual shirt (as seen in FIGS. 1A, 1B, 1C), a dress shirt, a turtleneck, an undershirt (as seen in FIGS. 5A, 5B, 5C), a sweater (as seen in FIGS. 4A, 4B, 4C), and the like.

According to some embodiments, shirt 10 comprises a collar 11, yoke 12, bodice 13, and one or more sleeve(s) 14. According to some embodiments, shirt 10 comprises a right sleeve 14*a* and/or left sleeve 14*b*. According to some embodiments, collar 11 encompasses the neck area of a subject's body. According to some embodiments, the yoke 12 encompasses the chest, shoulders, and upper back of a subject's body. According to some embodiments, bodice 13 encompasses the abdomen and back of a subject's body. According to some embodiments, sleeve(s) 14 encompasses the arm(s) of a subject's body, wherein the right sleeve 14*a* encompasses the right arm and the left sleeve 14*b* encompasses the right arm.

Shirt 10 as a whole or as each component part, collar 11, yoke 12, bodice 13, and sleeves 14*a* and 14*b*, can be provided with particular features, such as, being formed of a suitable material or fabric; and such as being formed in any suitable shape, length, width, and height.

As seen in FIGS. 1A, 1B, 1C, 3A, 3B, 3C, 4A, 4B, 4C, 5A, 5B, and 5C, according to some embodiments, a closeable opening 2 can be formed in any location on shirt 10 suitable to access a PAS on the upper body of a subject, for example, opening 2 can be formed in the inner surface, outer surface, right, left, lateral, medial, anterior, posterior, superior, inferior, proximal, and/or distal portion of shirt 10.

According to some embodiments, opening 2 can be positioned on the outer surface of the right side of collar 11. According to some embodiments, opening 2 can be positioned on the outer surface of the left side of collar 11. According to some embodiments, opening 2 can be positioned on the outer surface of the anterior portion of collar 11. According to some embodiments, opening 2 can be positioned on the outer surface of the posterior portion of collar 11. According to some embodiments, opening 2 can be positioned on the outer surface of the lateral portion of collar 11. According to some embodiments, opening 2 can be positioned on the outer surface of the medial portion of collar 11. According to some embodiments, opening 2 can be positioned on the outer surface of the superior portion of collar 11. According to some embodiments, opening 2 can be positioned on the outer surface of the inferior portion of collar 11.

According to some embodiments, opening 2 can be positioned on the outer surface of the right side of yoke 12. According to some embodiments, opening 2 can be positioned on the outer surface of the left side of yoke 12. According to some embodiments, opening 2 can be positioned on the outer surface of the anterior portion of yoke 12. According to some embodiments, opening 2 can be positioned on the outer surface of the posterior portion of yoke 12. According to some embodiments, opening 2 can be positioned on the outer surface of the lateral portion of yoke 12. According to some embodiments, opening 2 can be positioned on the outer surface of the medial portion of yoke 12. According to some embodiments, opening 2 can be positioned on the outer surface of the superior portion of yoke 12. According to some embodiments, opening 2 can be positioned on the outer surface of the inferior portion of yoke 12.

According to some embodiments, opening 2 can be positioned on the outer surface of the right side of bodice 13. According to some embodiments, opening 2 can be positioned on the outer surface of the left side of bodice 13. According to some embodiments, opening 2 can be positioned on the outer surface of the anterior portion of bodice 13. According to some embodiments, opening 2 can be positioned on the outer surface of the posterior portion of bodice 13. According to some embodiments, opening 2 can be positioned on the outer surface of the lateral portion of bodice 13. According to some embodiments, opening 2 can be positioned on the outer surface of the medial portion of bodice 13. According to some embodiments, opening 2 can be positioned on the outer surface of the superior portion of bodice 13. According to some embodiments, opening 2 can be positioned on the outer surface of the inferior portion of bodice 13.

According to some embodiments, an opening 2 can be formed in sleeve or sleeves 14. According to some embodiments, an opening 2 can be positioned on the outer surface of the distal portion of sleeve 14. According to some embodiments, an opening 2 can be positioned on the outer surface of the proximal portion of sleeve 14. According to some embodiments, an opening 2 can be positioned on the outer surface of right sleeve 14a. According to some embodiments, an opening 2 can be positioned on the outer surface of left sleeve 14b. According to some embodiments, an opening 2 can be positioned on the outer surface of the distal portion of right sleeve 14a. According to some embodiments, an opening 2 can be positioned on the outer surface of the distal portion of left sleeve 14b. According to some embodiments, an opening 2 can be positioned on the outer surface of the proximal portion of right sleeve 14a. According to some embodiments, an opening 2 can be positioned on the outer surface of the proximal portion of left sleeve 14b.

If the subject's arms and hands are in supination position, according to some embodiments an opening 2 can be positioned on the outer surface of the lateral, medial, anterior, and/or posterior portion of right sleeve 14a and/or left sleeve 14b. If the subject's arms and hands are in pronation position, according to some embodiments an opening 2 can be positioned on the outer surface of the lateral, medial, anterior, and/or posterior portion of left sleeve 14b.

As seen in FIGS. 3A, 3B, and 3C, according to some embodiments, facilitating member 4 can be positioned on any location on shirt 10 suitable to facilitate the utilization of a PAS on the upper body of a subject, for example, facilitating member 4 can be positioned on the inner surface, outer surface, right, left, lateral, medial, anterior, posterior, superior, inferior, proximal, and/or distal portion of shirt 10.

According to some embodiments, a facilitating member 4 can be positioned on the inner surface of the right side of collar 11. According to some embodiments, a facilitating member 4 can be positioned on the inner surface of the left side of collar 11. According to some embodiments, a facilitating member 4 can be positioned on the inner surface of the anterior portion of collar 11. According to some embodiments, a facilitating member 4 can be positioned on the inner surface of the posterior portion of collar 11. According to some embodiments, a facilitating member 4 can be positioned on the inner surface of the lateral portion of collar 11. According to some embodiments, a facilitating member 4 can be positioned on the inner surface of the medial portion of collar 11. According to some embodiments, a facilitating member 4 can be positioned on the inner surface of the superior portion of collar 11. According to some embodiments, facilitating member 4 can be positioned on the inner surface of the inferior portion of collar 11.

According to some embodiments, a facilitating member 4 can be positioned on the inner surface of the right side of yoke 12. According to some embodiments, a facilitating member 4 can be positioned on the inner surface of the left side of yoke 12. According to some embodiments, a facilitating member 4 can be positioned on the inner surface of the anterior portion of yoke 12. According to some embodiments, a facilitating member 4 can be positioned on the inner surface of the posterior portion of yoke 12. According to some embodiments, a facilitating member 4 can be positioned on the inner surface of the lateral portion of yoke 12. According to some embodiments, a facilitating member 4 can be positioned on the inner surface of the medial portion of yoke 12. According to some embodiments, a facilitating member 4 can be positioned on the inner surface of the superior portion of yoke 12. According to some embodiments, a facilitating member 4 can be positioned on the inner surface of the inferior portion of yoke 12.

According to some embodiments, a facilitating member 4 can be positioned on the inner surface of the right side of bodice 13. According to some embodiments, a facilitating member 4 can be positioned on the inner surface of the left side of bodice 13. According to some embodiments, a facilitating member 4 can be positioned on the inner surface of the anterior portion of bodice 13. According to some embodiments, a facilitating member 4 can be positioned on the inner surface of the posterior portion of bodice 13. According to some embodiments, a facilitating member 4 can be positioned on the inner surface of the lateral portion of bodice 13. According to some embodiments, a facilitating member 4 can be positioned on the inner surface of the medial portion of bodice 13. According to some embodiments, a facilitating member 4 can be positioned on the inner surface of the superior portion of bodice 13. According to some embodiments, a facilitating member 4 can be positioned on the inner surface of the inferior portion of bodice 13.

According to some embodiments, a facilitating member 4 can positioned on the inner surface of sleeve or sleeves 14. According to some embodiments, facilitating member 4 can be positioned on the inner surface of the distal portion of sleeve 14. According to some embodiments, facilitating member 4 can be positioned on the inner surface of the proximal portion of sleeve 14. According to some embodiments, a facilitating member 4 can be positioned on the inner surface of right sleeve 14a. According to some embodiments, an opening can be positioned on the inner surface of left sleeve 14b. According to some embodiments, a facilitating member 4 can be positioned on the inner surface of the distal portion of right sleeve 14a. According to some embodiments, a facilitating member 4 can be positioned on the inner surface of the distal portion of left sleeve 14b. According to some embodiments, a facilitating member 4 can be positioned on the inner surface of the proximal portion of right sleeve 14a. According to some embodiments, a facilitating member 4 can be positioned on the inner surface of the proximal portion of left sleeve 14b.

If the subject's arms and hands are in supination position, according to some embodiments facilitating member 4 can be positioned on the inner surface of the lateral, medial, anterior, and/or posterior portion of right sleeve 14*a* and/or left sleeve 14*b*. If the subject's arms and hands are in pronation position, according to some embodiments an facilitating member 4 can be positioned on the inner surface of the lateral, medial, anterior, and/or posterior portion of right sleeve 14*a* and/or left sleeve 14*b*.

According to some embodiments, shirt 10 can be formed by any technique suitable, such as, looming, molding, casting, machining, or by any known method to create the desired structure. Shirt 10 can formed as a unitary structure or as component pieces attached together by attachment means, such as adhesives, bonding, stitching, or machining.

Easy Access Trousers

As seen in FIGS. 2A, 2B, 2C, 6A, 6B, 6C, 7A, 7B, 7C, 8A, 8B, and 8C, according to some embodiments, the garment 1 is trousers 20 wherein the easy access apparel comprises
  i. trousers 20;
  ii. at least one closeable opening 2, comprising at least one fastener 3; and
  iii. at least one facilitating member 4.

Figure 8C:
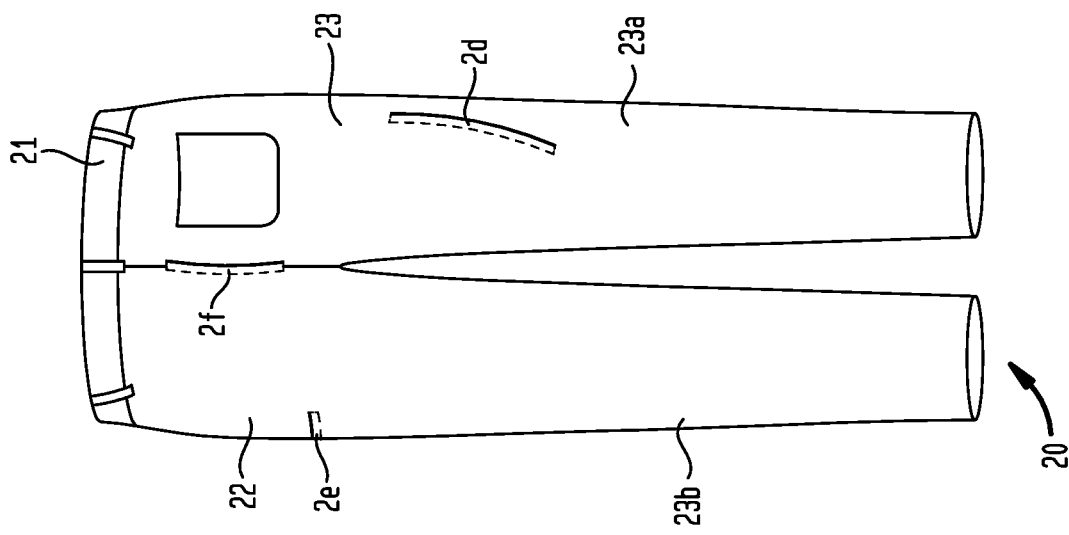
FIGS. 8A, 8B, 8C are front, side, and back plan views of an embodiment of the Easy Access Apparel of the present invention adapted for use as an Easy Access Trousers showing various positioning of at least one closeable opening(s) where
Figure 8B:
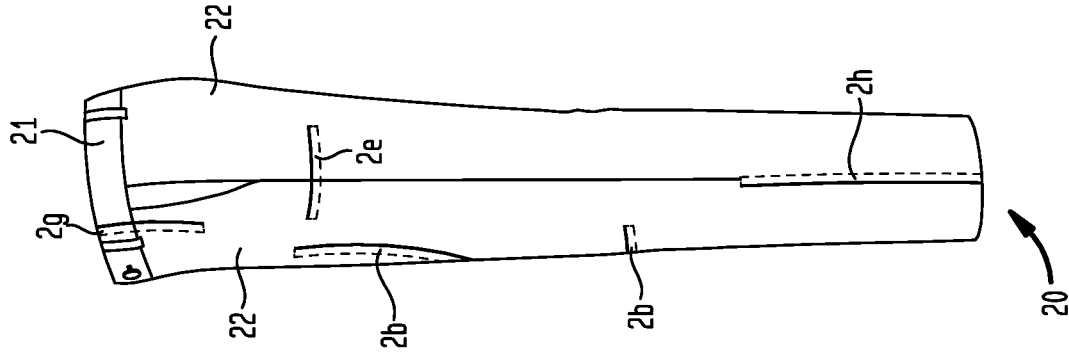
Figure 8A:
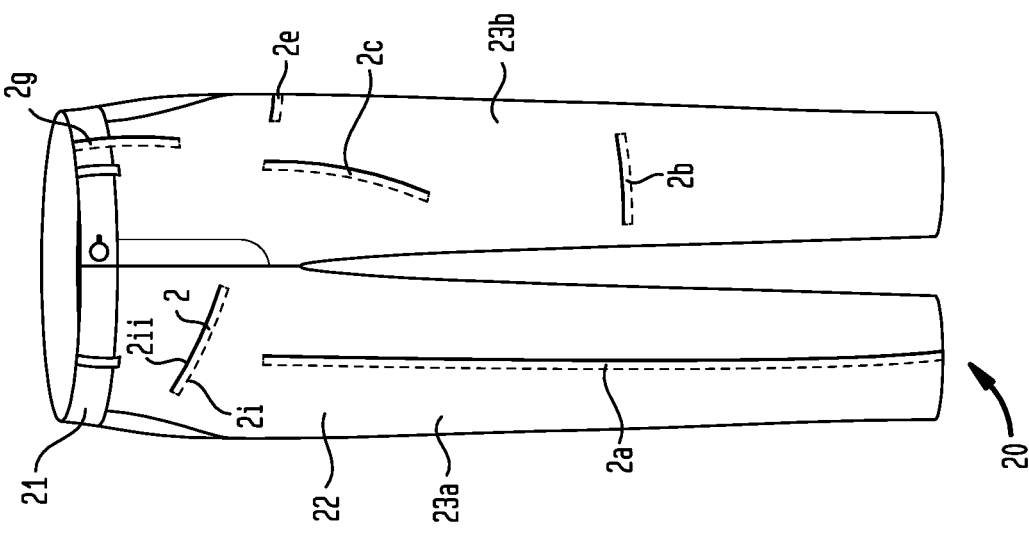

According to some embodiments, trousers 20 are any type of trousers that are constructed to encompass the lower body of a subject. According to some embodiments, trousers 20 can be any type of trousers such as sweatpants (as seen in FIGS. 6A, 6B, 6C), casual pants, dress pants (as seen in FIGS. 8A, 8B, 8C), leggings, short pants, and the like.

According to some embodiments, trousers 20 comprise a waistband 21, crotch-seat area 22, and one or more pant-leg(s) 23. According to some embodiments, trousers 20 comprise a right pant-leg 23*a* and/or a left pant-leg 23*b*. According to some embodiments, waistband 21 encompasses the waist of a subject's body. According to some embodiments, the crotch-seat area 22 encompasses the groin, crotch, and seat of a subject's body. According to some embodiments, pant-leg(s) 23 encompasses the legs(s) of a subject's body, wherein the right pant-leg 23*a* encompasses the right leg and the left pant-leg 23*b* encompasses the left leg.

Trousers 20 as a whole or as each component part, waistband 21, crotch-seat area 22, and pant-legs 23*a* and 23*b*, can be provided with particular features, such as, being formed of a suitable material or fabric; and such as being formed of a suitable shape, length, width, and height.

As seen in FIGS. 6A, 6B, 6C, 7A, 7B, 7C, 8A, 8B, and 8C, according to some embodiments a closeable opening 2 can be formed in any location on trousers 20 suitable to access a PAS on the lower body of a subject, for example, opening 2 can be formed in the inner surface, outer surface, right, left, lateral, medial, anterior, posterior, superior, inferior, proximal, and/or distal portion of trousers 20.

According to some embodiments, opening 2 can be positioned on the outer surface of the right side of waistband 21. According to some embodiments, opening 2 can be positioned on the outer surface of the left side of waistband 21. According to some embodiments, opening 2 can be positioned on the outer surface of the anterior portion of waistband 21. According to some embodiments, opening 2 can be positioned on the outer surface of the posterior portion of waistband 21. According to some embodiments, opening 2 can be positioned on the outer surface of the lateral portion of waistband 21. According to some embodiments, opening 2 can be positioned on the outer surface of the medial portion of waistband 21. According to some embodiments, opening 2 can be positioned on the outer surface of the superior portion of waistband 21. According to some embodiments, opening 2 can be positioned on the outer surface of the inferior portion of waistband 21.

According to some embodiments, opening 2 can be positioned on the outer surface of the right side of crotch-seat area 22. According to some embodiments, opening 2 can be positioned on the outer surface of the left side of crotch-seat area 22. According to some embodiments, opening 2 can be positioned on the outer surface of the anterior portion of crotch-seat area 22. According to some embodiments, opening 2 can be positioned on the outer surface of the posterior portion of crotch-seat area 22. According to some embodiments, opening 2 can be positioned on the outer surface of the lateral portion of crotch-seat area 22. According to some embodiments, opening 2 can be positioned on the outer surface of the medial portion of crotch-seat area 22. According to some embodiments, opening 2 can be positioned on the outer surface of the superior portion of crotch-seat area 22. According to some embodiments, opening 2 can be positioned on the outer surface of the inferior portion of crotch-seat area 22.

According to some embodiments, an opening 2 can be formed in pant-leg or pant-legs 23. According to some embodiments, an opening 2 can be positioned on the outer surface of the distal portion of pant-leg(s) 23. According to some embodiments, an opening 2 can be positioned on the outer surface of the proximal portion of pant-leg(s) 23. According to some embodiments, an opening 2 can be positioned on the outer surface of right pant-leg 23*a*. According to some embodiments, an opening can be positioned on the outer surface of left pant-leg 23*b*. According to some embodiments, an opening 2 can be positioned on the outer surface of the distal portion of right pant-leg 23*a*. According to some embodiments, an opening 2 can be positioned on the outer surface of the distal portion of left pant-leg 23*b*. According to some embodiments, an opening 2 can be positioned on the outer surface of the proximal portion of right pant-leg 23*a*. According to some embodiments, an opening 2 can be positioned on the outer surface of the proximal portion of left pant-leg 23*b*.

If the subject's legs and feet are in supination position, according to some embodiments an opening 2 can be positioned on the outer surface of the lateral, medial, anterior, and/or posterior portion of right pant-leg 23*a* and/or left pant-leg 23*b*. If the subject's legs and feet are in pronation position, according to some embodiments an opening 2 can be positioned on the outer surface of the lateral, medial, anterior, and/or posterior portion of right pant-leg 23*a* and/or left pant-leg 23*b*.

Figure 7C:
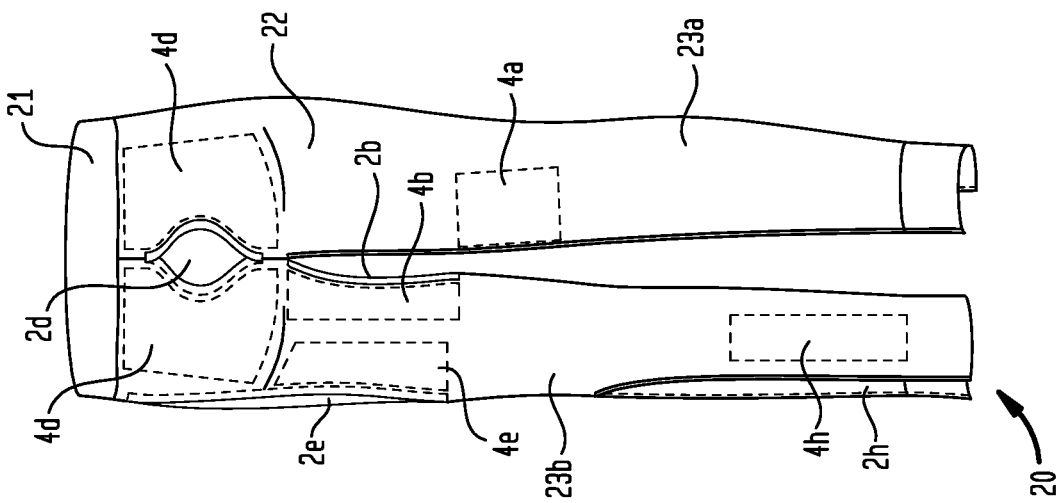
FIGS. 7A, 7B, 7C are front, side, and back plan views of an embodiment of the Easy Access Apparel of the present invention adapted for use as an Easy Access Trousers showing various positioning of at least one closeable opening(s) and various positioning of at least one facilitating member(s) where
Figure 7B:
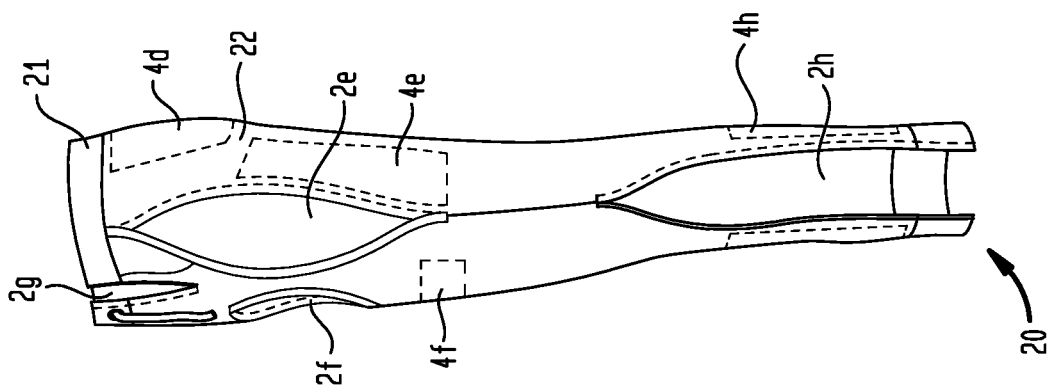
Figure 7A:
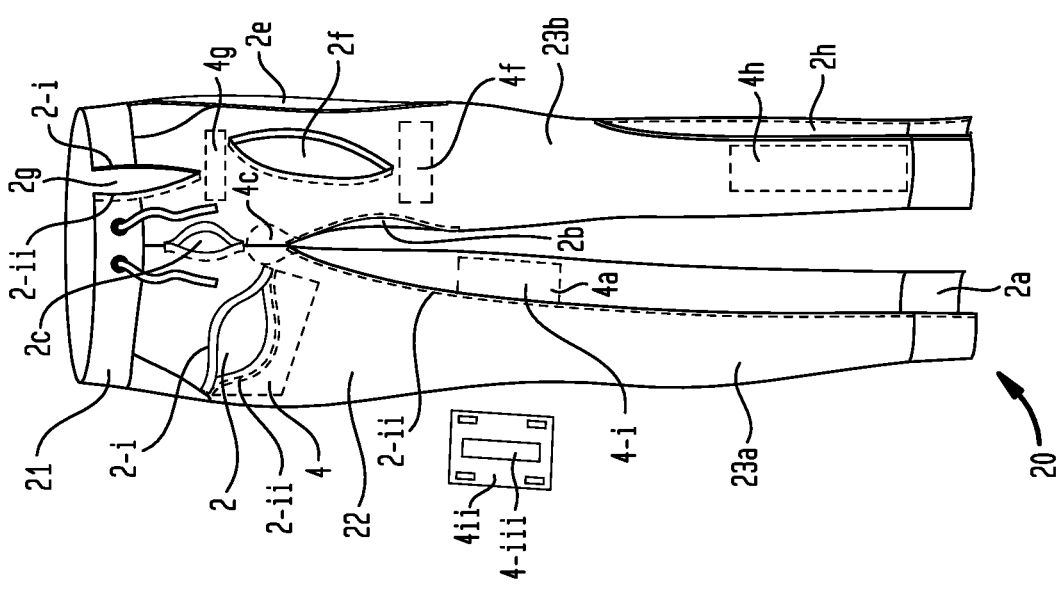

As seen in FIGS. 7A, 7B, and 7C, according to some embodiments a facilitating member 4 can be positioned on any location on trousers 20 suitable to facilitate the utilization of a PAS on the lower body of a subject, for example, facilitating member 4 can be positioned on the inner surface, outer surface, right, left, lateral, medial, anterior, posterior, superior, inferior, proximal, and/or distal portion of trousers 20.

According to some embodiments, a facilitating member 4 can be positioned on the inner surface of the right side of waistband 21. According to some embodiments, a facilitating member 4 can be positioned on the inner surface of the left side of waistband 21. According to some embodiments, a facilitating member 4 can be positioned on the inner surface of the anterior portion of waistband 21. According to some embodiments, a facilitating member 4 can be positioned on the inner surface of the posterior portion of waistband 21. According to some embodiments, a facilitating member 4 can be positioned on the inner surface of the lateral portion of waistband 21. According to some embodiments, a facilitating member 4 can be positioned on the inner surface of the medial portion of waistband 21. According to some embodiments, a facilitating member 4 can be positioned on the inner surface of the superior portion of waistband 21. According to some embodiments, a facilitating member 4 can be positioned on the inner surface of the inferior portion of waistband 21.

According to some embodiments, a facilitating member 4 can be positioned on the inner surface of the right side of crotch-seat area 22. According to some embodiments, a facilitating member 4 can be positioned on the inner surface of the left side of crotch-seat area 22. According to some embodiments, a facilitating member 4 can be positioned on the inner surface of the anterior portion of crotch-seat area 22. According to some embodiments, a facilitating member 4 can be positioned on the inner surface of the posterior portion of crotch-seat area 22. According to some embodiments, a facilitating member 4 can be positioned on the inner surface of the lateral portion of crotch-seat area 22. According to some embodiments, a facilitating member 4 can be positioned on the inner surface of the medial portion of crotch-seat area 22. According to some embodiments, a facilitating member 4 can be positioned on the inner surface of the superior portion of crotch-seat area 22. According to some embodiments, facilitating member 4 can be positioned on the inner surface of the inferior portion of crotch-seat area 22.

According to some embodiments, a facilitating member 4 can be positioned on pant-leg or pant-legs 23. According to some embodiments, a facilitating member 4 can be positioned on the inner surface of the distal portion of pant-leg(s) 23. According to some embodiments, a facilitating member 4 can be positioned on the inner surface of the proximal portion of pant-leg(s) 23. According to some embodiments, a facilitating member 4 can be positioned on the inner surface of right pant-leg 23a. According to some embodiments, an opening can be positioned on the inner surface of left pant-leg 23b. According to some embodiments, an facilitating member 4 can be positioned on the inner surface of the distal portion of right pant-leg 23a. According to some embodiments, a facilitating member 4 can be positioned on the inner surface of the distal portion of left pant-leg 23b. According to some embodiments, a facilitating member 4 can be positioned on the inner surface of the proximal portion of right pant-leg 23a. According to some embodiments, a facilitating member 4 can be positioned on the inner surface of the proximal portion of left pant-leg 23b.

If the subject's legs and feet are in supination position, according to some embodiments facilitating member 4 can be positioned on the inner surface of the lateral, medial, anterior, and/or posterior portion of right pant-leg 23a and/or left pant-leg 23b. If the subject's legs and feet are in pronation position, according to some embodiments facilitating member 4 can be positioned on the inner surface of the lateral, medial, anterior, and/or posterior portion of right pant-leg 23a and/or left pant-leg 23b.

According to some embodiments, trousers 20 can be formed by any technique suitable, such as, machining, and can be formed as a unitary piece or as component pieces attached together by attachment means, such as adhesives, bonding, sewing, or machining.

Easy Access Underwear

As seen in FIGS. 2A, 2B, 2C, 9A, 9B, and 9C, according to some embodiments, the garment 1 is underwear 30 wherein the easy access apparel comprises
i. underwear 30;
ii. at least one closeable opening 2, comprising at least one fastener 3; and
iii. at least one facilitating member 4.

According to some embodiments, underwear 30 is any type of garment that are constructed to encompass a portion of the lower body of a subject. According to some embodiments, underwear 30 can be any type of underwear such as bikinis, boxers, briefs or panties (as seen in FIGS. 9A, 9B, 9C), boy-shorts, jockstraps, thongs, and the like.

According to some embodiments, underwear 30 comprises a waistband 31, crotch-seat area 32, and one or more leg-hole(s) 33. According to some embodiments, underwear 30 comprises a anterior side and a posterior side. According to some embodiments, underwear 30 comprises a right leg-hole 33a and/or a left leg-hole 33b. According to some embodiments, waistband 31 encompasses the waist of a subject's body. According to some embodiments, the crotch-seat area 32 encompasses the groin, crotch, and seat of a subject's body. According to some embodiments, leg-hole(s) 33 encompasses the leg(s) of a subject's body, wherein the right leg-hole 33a encompasses the right leg and the left leg-hole 33b encompasses the left leg.

Underwear 30 as a whole or as each component part, waistband 31, crotch-seat area 32, and leg-holes 33a and 33b, can be provided with particular features, such as, being formed of a suitable material or fabric; and such as being formed of a suitable shape, length, width, and height.

Figure 9A:
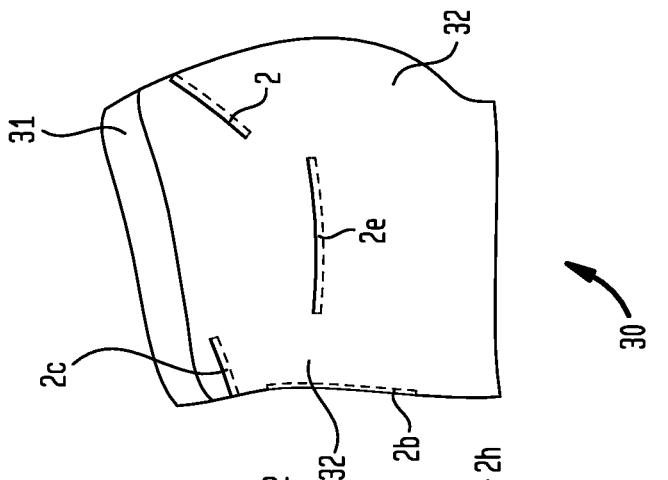
FIGS. 9A, 9B, 9C are front, side, and back plan views of an embodiment of the Easy Access Apparel of the present invention adapted for use as an Easy Access Underwear showing various positioning of at least one closeable opening(s) where
Figure 9B:
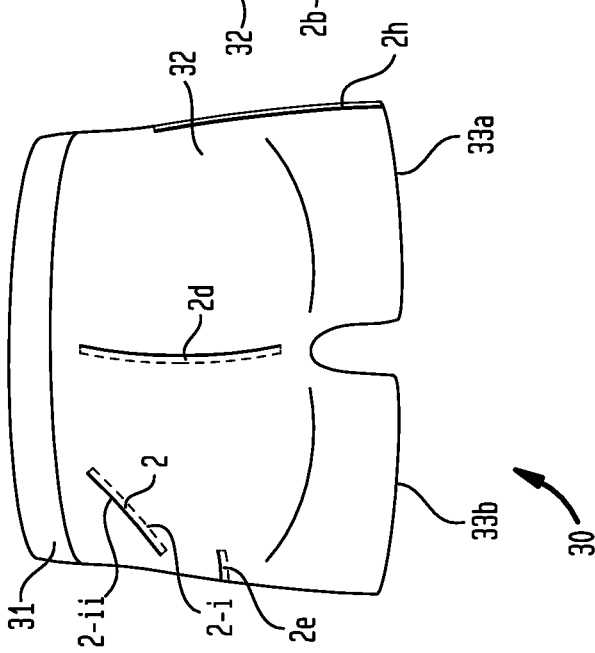
Figure 9C:
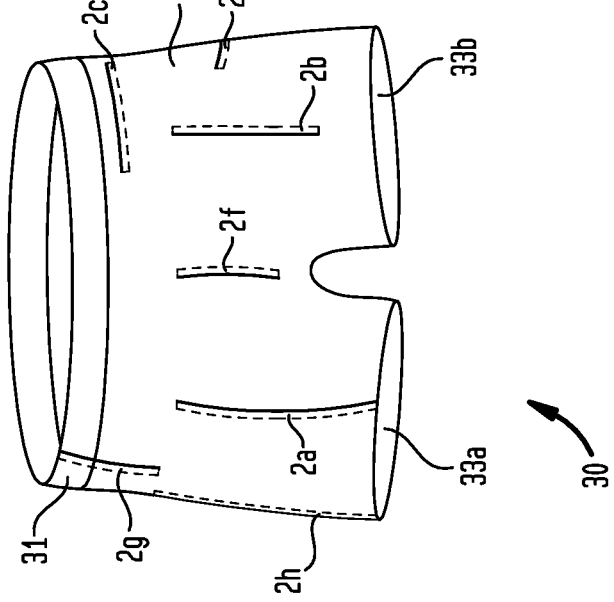

As seen in FIGS. 9A, 9B, and 9C according to some embodiments, a closeable opening 2 can be formed in any location on underwear 30 suitable to access a PAS on the lower body of a subject, for example, opening 2 can be formed in the inner surface, outer surface, right, left, lateral, medial, anterior, posterior, superior, inferior, proximal, and/or distal portion of underwear 30.

According to some embodiments, opening 2 can be positioned on the outer surface of the right side of waistband 31. According to some embodiments, opening 2 can be positioned on the outer surface of the left side of waistband 31. According to some embodiments, opening 2 can be positioned on the outer surface of the anterior portion of waistband 31. According to some embodiments, opening 2 can be positioned on the outer surface of the posterior portion of waistband 31. According to some embodiments, opening 2 can be positioned on the outer surface of the lateral portion of waistband 31. According to some embodiments, opening 2 can be positioned on the outer surface of the medial portion of waistband 31. According to some embodiments, opening 2 can be positioned on the outer surface of the superior portion of waistband 31. According to some embodiments, opening 2 can be positioned on the outer surface of the inferior portion of waistband 31.

According to some embodiments, opening 2 can be positioned on the outer surface of the right side of crotch-seat area 32. According to some embodiments, opening 2 can be positioned on the outer surface of the left side of crotch-seat area 32. According to some embodiments, opening 2 can be positioned on the outer surface of the anterior portion of crotch-seat area 32. According to some embodiments, opening 2 can be positioned on the outer surface of the posterior portion of crotch-seat area 32. According to some embodiments, opening 2 can be positioned on the outer surface of the lateral portion of crotch-seat area 32. According to some embodiments, opening 2 can be positioned on the outer surface of the medial portion of crotch-seat area 32. According to some embodiments, opening 2 can be positioned on the outer surface of the superior portion of crotch-seat area 32. According to some embodiments, opening 2 can be positioned on the outer surface of the inferior portion of crotch-seat area 32.

According to some embodiments, an opening 2 can be formed in leg-hole or leg-holes 33. According to some embodiments, an opening 2 can be positioned on the outer surface of the distal portion of leg-hole(s) 33. According to some embodiments, an opening 2 can be positioned on the outer surface of the proximal portion of right leg-hole 33a. According to some embodiments, an opening 2 can be positioned on the outer surface of left leg-hole 33b. According to some embodiments, an opening can be positioned on the outer surface of left leg-hole 33b. According to some embodiments, an opening 2 can be positioned on the outer surface of the distal portion of right leg-hole 33a. According to some embodiments, an opening 2 can be positioned on the outer surface of the distal portion of left leg-hole 33b. According to some embodiments, an opening 2 can be positioned on the outer surface of the proximal portion of right leg-hole 33a. According to some embodiments, an opening 2 can be positioned on the outer surface of the proximal portion of left leg-hole 33b.

If the subject's feet and legs are in supination position, according to some embodiments an opening 2 can be positioned on the outer surface of the lateral, medial, anterior, and/or posterior portion of right leg-hole 33a and/or left leg-hole 33b. If the subject's feet and legs are in pronation position, according to some embodiments an opening 2 can be positioned on the outer surface of the lateral, medial, anterior, and/or posterior portion of right leg-hole 33a and/or left leg-hole 33b.

According to some embodiments, a facilitating member 4 can be formed in any location on underwear 30 suitable to facilitate the utilization of a PAS on the lower body of a subject, for example, a facilitating member 4 can be formed in the inner surface, outer surface, right, left, lateral, medial, anterior, posterior, superior, inferior, proximal, and/or distal portion of underwear 30.

According to some embodiments, a facilitating member 4 can be positioned on the inner surface of the right side of waistband 31. According to some embodiments, a facilitating member 4 can be positioned on the inner surface of the left side of waistband 31. According to some embodiments, a facilitating member 4 can be positioned on the inner surface of the anterior portion of waistband 31. According to some embodiments, a facilitating member 4 can be positioned on the inner surface of the posterior portion of waistband 31. According to some embodiments, a facilitating member 4 can be positioned on the inner surface of the lateral portion of waistband 31. According to some embodiments, a facilitating member 4 can be positioned on the inner surface of the medial portion of waistband 31. According to some embodiments, a facilitating member 4 can be positioned on the inner surface of the superior portion of waistband 31. According to some embodiments, a facilitating member 4 can be positioned on the inner surface of the inferior portion of waistband 31.

According to some embodiments, a facilitating member 4 can be positioned on the inner surface of the right side of crotch-seat area 32. According to some embodiments, a facilitating member 4 can be positioned on the inner surface of the left side of crotch-seat area 32. According to some embodiments, a facilitating member 4 can be positioned on the inner surface of the anterior portion of crotch-seat area 32. According to some embodiments, a facilitating member 4 can be positioned on the inner surface of the posterior portion of crotch-seat area 32. According to some embodiments, a facilitating member 4 can be positioned on the inner surface of the lateral portion of crotch-seat area 32. According to some embodiments, a facilitating member 4 can be positioned on the inner surface of the medial portion of crotch-seat area 32. According to some embodiments, a facilitating member 4 can be positioned on the inner surface of the superior portion of crotch-seat area 32. According to some embodiments, a facilitating member 4 can be positioned on the inner surface of the inferior portion of crotch-seat area 32.

According to some embodiments, a facilitating member 4 can be positioned on the inner surface of leg-hole or leg-holes 33. According to some embodiments, a facilitating member 4 can be positioned on the inner surface of the distal portion of leg-hole(s) 33. According to some embodiments, a facilitating member 4 can be positioned on the inner surface of the proximal portion of right leg-hole 33a. According to some embodiments, a facilitating member 4 can be positioned on the inner surface of left leg-hole 33b. According to some embodiments, an opening can be positioned on the inner surface of left leg-hole 33b. According to some embodiments, a facilitating member 4 can be positioned on the inner surface of the distal portion of right leg-hole 33a. According to some embodiments, a facilitating member 4 can be positioned on the inner surface of the distal portion of left leg-hole 33b. According to some embodiments, a facilitating member 4 can be positioned on the inner surface of the proximal portion of right leg-hole 33a. According to some embodiments, a facilitating member 4 can be positioned on the inner surface of the proximal portion of left leg-hole 33b.

If the subject's feet and legs are in supination position, according to some embodiments facilitating member 4 can be positioned on the inner surface of the lateral, medial, anterior, and/or posterior portion of right leg-hole 33a and/or left leg-hole 33b. If the subject's feet and legs are in pronation position, according to some embodiments facilitating member 4 can be positioned on the inner surface of the lateral, medial, anterior, and/or posterior portion of right leg-hole 33a and/or left leg-hole 33b.

According to some embodiments, underwear 30 can be formed by any technique suitable, such as, by molding, casting, machining, bonding, sewing or stitching, and can be formed as a unitary piece or as component pieces attached together by attachment means, such as adhesives, bonding, sewing, or machining.

Methods of Use

The described easy access apparel is useful for enhancing and/or maintaining the comfort of a subject during PAS utilization. The method for enhancing and/or maintain the comfort of a subject comprises the step of providing a subject with an easy access apparel comprised of a garment, the garment comprising at least one closeable opening, at least one fastener; and at least one facilitating member. As used herein, the phrase "maintaining or enhancing the comfort of a subject" can be used to describe any physical, environmental or emotional factor, the satisfaction of which promotes a state of well-being.

For example, according to some embodiments, the described invention can maintain or enhance physical comfort during PAS access. Physical comfort can be maintained or enhanced by retaining, reducing, or increasing the subject's body temperature during PAS utilization.

According to some embodiments, the described invention can maintain or enhance environmental comfort during PAS utilization. Environmental comfort can be maintained or enhanced, for example, by preventing or limiting the feeling of discomfort associated with sitting or reclining for extended periods of time during utilization of a PAS by providing the garment of the described invention with features such as being formed from soft material.

According to some embodiments the described invention can maintain or enhance emotional comfort during PAS utilization. Emotional comfort can be maintained or enhanced, for example, by maintaining and increasing a subject's modesty by providing the garment of the described invention with features such as reducing the amount of skin exposed during utilization of PAS. According to some embodiments, emotional comfort can be maintained or enhanced by maintain or increasing a subject's dignity, feelings of humanization, normalization, and/or destigimatization by providing the garment of the described invention with features that allow the apparel to be worn in every day settings outside of PAS utilization settings.

According to some embodiments, the methods of the present invention can be effective to enhance or maintain the comfort of a subject during PAS utilization by at least 1%, by at least 5%, by at least 10%, by at least 15%, by at least 20%, by at least 25%, by at least 30%, by at least 35%, by at least 40%, by at least 45%, or by at least 50% when compared to a subject in similar medical circumstances that is not provided with the easy access apparel thereof ("a control").

All referenced journal articles, patents, and other publications are incorporated by reference herein in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Easy Access Henley

A shirt-type easy access apparel is constructed as a long-sleeve Henley shirt.

Opening and Zipper Placements Specifications: Right Sleeve—a 22 inch long opening is formed on the anterior side of the right sleeve at 1.5 inch from center of sleeve and 1 inch from shoulder seam at the most proximal end of the sleeve, and runs the length of the sleeve to the most distal portion of the sleeve at the cuff. Yoke—a 14 inch opening is formed on the anterior portion of the left-side of the yoke at 4.5 inches from the shoulder seam, at a 125° angle relative to the superior end of the shirt. Zippers are attached to both opening individually so that openings can be respectively unzipped open, and zipped shut.

Facilitating Member Placement Specifications: Right Sleeve—a first 3¾ inch wide Velcro® strip is sewn onto the inner surface of the dorsal portion of the right sleeve across from the opening, starting 6 inches from the shoulder seam at the most proximal end of the sleeve in a parallel direction to the opening and extends to the most distal end of the sleeve at the cuff. A second 3¾ inch Velcro® strip is sewn onto the inner surface of the dorsal portion of the right sleeve across from the opening, starting 12 inches from the shoulder seam and runs perpendicular to the first strip and opening.

Example 2. Easy Access Sweater

A shirt-type easy access apparel is constructed as a long-sleeve hooded sweatshirt.

Opening and Zipper Placements Specifications: Yoke—a 14 inch opening is formed on the anterior portion of the left-side of the yoke at 4.5 inches from the shoulder seam at the most proximal end of the sleeve, towards the inferior end of the bodice of the shirt at a 125° angle relative to the superior end of the shirt. A zipper system is attached to the opening so that the opening can be respectively unzipped open, and zipped shut.

Example 3. Easy Access Sweatpants

A trousers-type easy access apparel is constructed as a pair of sweatpants.

Opening and Zipper Placement Specifications: Right Pant Leg—a 20 inch opening is formed on the medial portion of the right pant-leg along the inseam starting from crotch seam at the most proximal end of the pant leg to the pant-cuff at the most distal end of the pant-leg. A zipper system is attached to the opening so that opening can be respectively unzipped open, and zipped shut.

Facilitating Member Placement Specifications: a first 3¾ inch wide Velcro® strip is sewn onto the inner surface of the dorsal portion of the right pants-leg, starting 6 inches from the shoulder seam and runs in a parallel direction with the opening to leg cuff at the most distal end of the pant-leg. A second ¾ inch Velcro® strip is sewn onto the inner surface of the dorsal portion of the pant leg, starting 12 inches from the crotch seam and runs perpendicular to the first strip and opening.

Example 4. Evaluation of Enhancement or Maintenance of Comfort

Evaluation of the easy access apparel of the described invention will be performed in human volunteers wearing the easy access apparel described herein and will evaluate the level of comfort of a subject during PAS access.

Evaluations in the improvements in level of comfort may be based on qualitative descriptions of the subject's feelings of maintenance or enhancement of comfort, based on physical, environmental, or emotional factors, the satisfaction of which promotes a state of well-being.

For example, the volunteers may be divided into groups for each apparel type according to their PAS location, and a control group. The volunteers will be given their respective apparel prior to access to the PAS site and told to wear the apparel throughout PAS site access. Volunteers will then be asked to rank their physical, emotional, and environmental comfort level on a survey. Evaluations in improvements in comfort may be based on qualitative evaluation from test groups as compared to qualitative evaluation from the control group.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

The invention claimed is:

1. An easy access apparel for every day wear by a chronically ill subject who is undergoing chronic medical treatment, the easy access apparel comprising:
   a garment including an inner surface, an outer surface, a right side, a left side, an anterior portion, a posterior portion, a superior end, an inferior end, a lateral end, and a medial end, the garment comprising:
   (i) closeable openings each comprising at least one fastener, the closeable openings including a first opening formed in the right side of the garment, a second opening formed in left side of the garment, a third opening formed in the anterior portion of the garment, a fourth opening formed in the posterior portion of the garment, a fifth opening formed in a portion of the garment at or near the superior end of the garment, a sixth opening formed in a portion of the garment at or near the inferior end of the garment, a seventh opening formed in a portion of the garment at or near the lateral end of the garment, and an eighth opening formed in a portion of the garment at or near the medial end of the garment, wherein each of the closeable openings is continuously closeable along an entire length of the respective closeable openings;
   (ii) at least one facilitating object configured to hold a device in place for accessing a percutaneous access site on the body of a subject accessible through at least one of the closeable openings;
   (iii) a hook-and-loop fastening system including a plurality of first components and at least a second component, wherein each of the closeable openings has an associated first component of the plurality of first components attached to the inner surface of the garment at or near each of the closeable openings, the at least one second component located on the at least one facilitating object for attachment of the at least one facilitating object to the inner surface of the garment, wherein the at least one facilitating object is positioned on the inner surface of the right side, the left side, the anterior portion, the posterior portion, the superior end, the inferior end, the lateral end, and/or the medial end of the garment; and
   (iv) a facilitating area formed on the garment adjacent to at least one of the closeable openings to facilitate use of the percutaneous access site on the body of the subject;
   wherein the at least one facilitating object is adapted to facilitate utilization of the percutaneous access site on the body of a subject;
   wherein the apparel is adapted to increase the physical, environmental, and emotional comfort of the subject;
   wherein each of the closeable openings is formed on the outer surface of the garment through to the inner surface of the garment; and
   wherein:
   (a) at least one of the closeable openings is positioned over the percutaneous access site on the body of the subject when the easy access apparel is worn by the subject, a first garment edge and a second garment edge surrounding the at least one of the closeable openings;
   (b) a noncontiguous alignment of the first garment edge and the second garment edge is adapted to open the closeable openings and expose the percutaneous access site when the easy access apparel is worn by the subject, and the contiguous alignment of the first garment edge and the second garment edge is adapted to close the closeable openings and conceal the percutaneous access site; and (c) the at least one fastener is a fastening system comprising a first fastening component and second fastening component, wherein the first fastening component is located on the first garment edge and the second fastening component is located on the second garment edge of the garment, the first garment edge and the second garment edge surrounding the closeable openings, and engagement of the first fastening component and the second fastening component results in the closing of the closeable openings, and disengagement of the first and second fastening components results in opening of the closeable openings.

2. The easy access apparel of claim 1, wherein the garment is a shirt, trousers, or underwear.

3. The easy access apparel of claim 1, wherein the at least one fastener is a zipper system.

4. The easy access apparel of claim 1, wherein the at least one facilitating object is a means for limiting, preventing, or stopping fluid leakage during the utilization of the percutaneous access site when the easy access apparel is worn by the subject.

5. The easy access apparel of claim 1, wherein the at least one facilitating object is an object configured to provide anti-microbial, anti-septic, and/or wound healing during the utilization of the percutaneous access site.

6. The easy access apparel of claim 1, wherein the at least one facilitating object comprises a sterile disposable absorbent article.

7. The easy access apparel of claim 6, wherein the disposable absorbent article comprises one or more selected from the group consisting of a flake, a strip, powders, filaments, fibers, a film, a coating, a textile, a nonwoven material, a napkin, a pad, a mat, a gauze, a dressing, a sponge, a bandage, or a foam.

8. The easy access apparel of claim 6, wherein the disposable absorbent article is sterilized gauze, or a sterilized pad.

9. The easy access apparel of claim 6, wherein the disposable absorbent article comprises one or more layers.

10. The easy access apparel of claim 9, wherein the disposable absorbent article comprises a first, second, and third layer, the first layer comprising a liquid permeable material, the second layer comprising a liquid absorbent material, and a third layer comprising a liquid impermeable layer.

11. The easy access apparel of claim 10, wherein:
a. the liquid permeable materials include textile and non-woven fabric, a perforated film forming polymer, a porous foam, a reticulated foam, a reticulated thermoplastic film or a thermoplastic scrims;
b. the liquid absorbent materials include comminuted wood pulp, creped cellulose cotton, an absorbent foam, an absorbent sponge, a synthetic staple fiber, a polymeric fiber, a hydrogel-forming polymer comprises a gelling agent, or a combination thereof; and
C. the liquid impermeable materials include polyethylene, polypropylene, polyester, a polyamide, ethylene vinyl acetate, polyvinyl chloride, polyvinylidene chloride, cellophane, nitrocellulose or a cellulose acetate film.

12. A method of improving the comfort of a subject during the utilization of a percutaneous access site, comprising:
providing an easy access apparel, the easy access apparel comprising:
a garment including an inner surface, an outer surface, a right side, a left side, an anterior portion, a posterior portion, a superior end, an inferior end, a lateral end, and a medial end, the garment comprising:
(i) closeable openings each comprising at least one fastener, the closeable openings including a first opening formed in the right side of the garment, a second opening formed in left side of the garment, a third opening formed in the anterior portion of the garment, a fourth opening formed in the posterior portion of the garment, a fifth opening formed in a portion of the garment at or near the superior end of the garment, a sixth opening formed in a portion of the garment at or near the inferior end of the garment, a seventh opening formed in a portion of the garment at or near the lateral end of the garment, and an eighth opening formed in a portion of the garment at or near the medial end of the garment, wherein each of the closeable openings is continuously closeable along its an entire length of the respective closeable openings;
(ii) at least one facilitating object configured to hold a device in place for accessing a percutaneous access site on the body of a subject accessible through at least one of the closeable openings;
(iii) a hook-and-loop fastening system including a plurality of first components and at least a second component, wherein each of the closeable openings has an associated first component of the plurality of first components attached to the inner surface of the garment at or near each of the closeable openings, the at least one second component located on the at least one facilitating object for attachment of the at least one facilitating object to the inner surface of the garment, wherein the at least one facilitating object is positioned on the inner surface of the right side, the left side, the anterior portion, the posterior portion, the superior end, the inferior end, the lateral end, and/or the medial end of the garment; and
(iv) a facilitating area formed on the garment adjacent to at least one of the closeable openings to facilitate use of the percutaneous access site on the body of the subject;
wherein the at least one facilitating object is adapted to facilitate utilization of the percutaneous access site on the body of a subject;
wherein the apparel is adapted to increase the physical, environmental, and emotional comfort of the subject;
wherein each of the closeable openings is formed on the outer surface of the garment through to the inner surface of the garment; and
wherein:
(a) at least one of the closeable openings is positioned over the percutaneous access site on the body of the subject when the easy access apparel is worn by the subject, a first garment edge and a second garment edge surrounding the at least one of the closeable openings;
(b) a noncontiguous alignment of first and second garment edges is adapted to open the closeable openings and expose the percutaneous access site when the easy access apparel is worn by the subject, and the contiguous alignment of the first garment edge and the second garment edge is adapted to close the closeable openings and conceal the percutaneous access site; and
(c) the at least one fastener is a fastening system comprising a first fastening component and second fastening component, wherein the first fastening component is located on the first garment edge and the second fastening component is located on the second garment edge of the garment, the first and second garment edges surrounding the closeable openings, and engagement of the first fastening component and the second fastening component results in the closing of the closeable openings, and disengagement of the first and second fastening components results in opening of the closeable openings.

13. The method of claim 12, wherein:
(a) the easy access apparel is effective to enhance or maintain the physical, environmental or emotional comfort of a subject; or
(b) the easy access apparel is effective to enhance or maintain a subject's perception of dignity; or
(c) the easy access apparel is effective to enhance or maintain a subject's sensation of modesty; or
(d) the easy access apparel is effective to enhance or maintain a subject's feeling of normalcy.

* * * * *